US007632918B2

(12) United States Patent
Chu et al.

(10) Patent No.: US 7,632,918 B2
(45) Date of Patent: Dec. 15, 2009

(54) SEMI-SYNTHETIC GLYCOPEPTIDES WITH ANTIBIOTIC ACTIVITY

(75) Inventors: Daniel Chu, Santa Clara, CA (US); Maria N. Preobrazhenskaya, Moscow (RU); Svetlana S. Printsevskaya, Moscow (RU); Eugenia N. Olsufyeva, Moscow (RU)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 290 days.

(21) Appl. No.: 11/361,852

(22) Filed: Feb. 24, 2006

(65) Prior Publication Data

US 2006/0276623 A1 Dec. 7, 2006

Related U.S. Application Data

(60) Provisional application No. 60/657,297, filed on Feb. 28, 2005.

(51) Int. Cl.
*A61K 38/14* (2006.01)

(52) U.S. Cl. ........................................................ 530/322

(58) Field of Classification Search ........................ None
See application file for complete search history.

(56) References Cited

U.S. PATENT DOCUMENTS

| | | | |
|---|---|---|---|
| 4,698,327 | A | 10/1987 | Nagarajan et al. |
| 5,488,131 | A | 1/1996 | Myers |
| 5,500,410 | A | 3/1996 | Malabarba et al. |
| 5,521,155 | A | 5/1996 | Malabarba et al. |
| 5,840,684 | A | 11/1998 | Cooper et al. |
| 5,977,062 | A | 11/1999 | Cooper et al. |
| 6,841,661 | B2 | 1/2005 | Kim et al. |
| 7,273,845 | B2 | 9/2007 | Zhao et al. |
| 7,368,422 | B2 | 5/2008 | Lei et al. |
| 7,348,309 | B2 | 7/2008 | Thorson |
| 2003/0008812 | A1 | 1/2003 | Christensen et al. |
| 2004/0136947 | A1 | 7/2004 | Zhao et al. |
| 2004/0259228 | A1 | 12/2004 | Thorson |
| 2006/0276623 | A1 | 12/2006 | Chu et al. |
| 2007/0021328 | A1 | 1/2007 | Lei et al. |

FOREIGN PATENT DOCUMENTS

| | | |
|---|---|---|
| EP | 0276740 | 8/1988 |
| EP | 0365319 | 4/1990 |
| EP | 036531 | 8/1995 |
| EP | 0667353 | 8/1995 |
| WO | WO00/59528 | 10/2000 |
| WO | WO 00/59528 | * 10/2000 |
| WO | WO00/69893 | 11/2000 |
| WO | WO01/58933 | 8/2001 |
| WO | WO01/81372 | 11/2001 |
| WO | WO 2004/019970 | * 3/2004 |
| WO | WO2004/019970 | 11/2004 |
| WO | WO2006/093933 | 9/2006 |
| WO | WO2006/094082 | 9/2006 |

OTHER PUBLICATIONS

Idogaki et al, "Preparation of (R)- and (S)-4-chloro-3-acetoxybutyronitrile using microbial resolution," Tetrahedron: Asymmetry vol. 12, Issue 3, Mar. 5, 2001, pp. 369-373.*

L3 Answer 6 of 7 Hcaplus Copyright 2009 ACS on STN atached as pdf file STN_Search_Reference.pdf pp. 1-4.*

PCT/US06/07049, International Search Report mailed Mar. 28, 2007.

PCT/US06/07049, Written Opinion mailed Mar. 28, 2007.

Berge et al., Journal of Pharmaceutical Sciences, vol. 66, No. 1, Jan. 1977, pp. 1-19.

Miroshnikova et al., "Structure-Activity Relationships in the Series of Eremomycin Carboxamides", The Journal Antibiotics, vol. 53, No. 3, Mar. 2000, pp. 286-291.

Pavlov et al., "A New Type of Chemical Modification of Glycopeptides Antibiotics: Aminomethylated Derivatives of Eremomycin and Their Antibacterial Activity", The Journal of Antibiotics, vol. 50, No. 6, Jun. 1997, pp. 509-513.

Pavlov et al., "Carboxamides and Hydrazide of Glycopeptide Antibiotic Eremomycin Synthesis and Antibacterial activity", The Journal of Antibiotics, vol. 39, No. 2, Feb. 1996, pp. 194-198.

Feliu. L. et al., *Cyclic Peptides Containing Biaryl and Biaryl Ether Linkages, International Journal of Peptide Research and Therapeutics*, vol. 11, No. 1, Mar. 2005, pp. 53-97.

Jia, Y. et al., *Identification of synthetic compounds active against VRE: the role of the lapidated aminoglucose and the structure of glycopeptide binding pocket, Bioorganic & Medicinal Chemistry Letters*, 15 (2005) 4594-4599.

Malabarba, A. et al., *Structural Modifications of Glycopeptide Antibiotics, Medicinal Research Reviews*, vol. 17, No. 1, (1997) 69-137.

Nagarajan, R. et al., *Synthesis and Antibacterial Activity of N-ACYL Vancomycins, The Journal of Antibiotics*, Oct. 1988, pp. 1430-1438.

U.S. Appl. No. 11/361,852, entitled *Semi-Synthetic Desmethyl-Vancomycin-Based Glycopeptides with Antibiotic Activity*, Chu et al., filed Feb. 24, 2006.

(Continued)

*Primary Examiner*—Cecilia Tsang
*Assistant Examiner*—Thomas S Heard
(74) *Attorney, Agent, or Firm*—Weaver Austin Villeneuve & Sampson LLP

(57) ABSTRACT

Semi-synthetic glycopeptides having antibacterial activity are based on modifications of the eremomycin, A82846B, vancomycin, teicoplanin, and A-40,926 scaffolds, in particular, acylation of the sugar moieties on these scaffolds with certain acyl groups; and/or conversion of an acid moiety on the macrocyclic ring of these scaffolds to certain substituted amides; or having a combination of an alkylation modification of the amino substituent on the amino-substituted sugar moiety on these scaffolds with certain alkyl groups or acylation modification of the amino substituent on the amino-substituted sugar moiety on this scaffold with certain alkyl groups, and conversion of the acid moiety on the macrocyclic ring of this scaffolds to certain substituted amides. Also provided are methods for the synthesis of the compounds, pharmaceutical compositions containing the compounds, and methods of use of the compounds for the treatment and/or prophylaxis of diseases, especially bacterial infections.

8 Claims, No Drawings

OTHER PUBLICATIONS

International patent application No. PCT/US06/07337, International Search Report dated Nov. 20, 2006.
International patent application No. PCT/US06/07337, Written Opinion dated Nov. 20, 2006.
U.S Office Action, for U.S. Appl. No. 11/361,682, mailed Jul. 11, 2008.
L. Boeck et al. J. Antibiotics (1984) 37(5), pp. 446-453.
H.-K. Han. AAPS Pharmsci. (2000) 2(1), article 6, pp. 1-11.
S.R. Vippagunta, et al. Adv. Drug Delivery Rev. (2001) 48, pp. 3-26.
P. Ettmayer et al., J. Med. Chem (2004) 47(10), pp. 2393-2404.
B. Testa. Biochem. Pharm (2004) 68, pp. 2097-2106.
J. March Organic Chemistry, 3rd Ed. (1985), pp. 66-70, 82-119 and 1024-1026.
Majumdar S. et al., Expert Opin. Drug Delivery (2006) 39(4), pp. 511-527.
U.S. Office Action for U.S. Appl. No. 10/525,784, mailed Jul. 25, 2008.
International Search Rpt for PCT/US06/07021, mailed Nov. 28, 2006.
International Written Opinion for PCT/US06/0721, mailed Nov. 28, 2006.
Notice of Allowance for U.S. Appl. No. 11/361,311, mailed Oct. 30, 2007.
U.S. Office Action for U.S. Appl. No. 11/361,311, mailed Mar. 22, 2007.
U.S. Final Office Action for U.S. Appl. No. 11/361,311, mailed Sep. 10, 2007.
International Search Rpt for PCT/2004/019970, mailed Jul. 22, 2004.
International Preliminary Examination Report for PCT/WO2004/019970, mailed Nov. 12, 2004.
Georgiou, Niki A et al: "The chemotherapeutic agent bleomycin in a two-drug combination with zidovudine, ritonavir or indinavir synergistically inhibits HIV Type-1 replication in peripheral blood lymphocytes", International Journal of Antimicrobial agents, vol. 18, No. 6 Dec. 2001, pp. 513-518.
Singh S. B. et al: "The complestatins as HIV-1 integrease inhibitors. Efficient isolation; structure elucidation, and inhibitory activities of isocomplestatin, chloropeptin I, new complestatins, A and B, and acid-hydrolysis products of chloropeptin I." Journal of Natural Products. US, Jul. 2001, vol. 64, No. 7, Jul. 2001, pp. 874-882.
Allen Norris E. et al.: "Hexapeptide derivatives of glycopeptide antibiotics: Tools for mechanism of action studies" Antimicrobial Agents and Chemotherapy, vol. 46, No. 8, Aug. 2002, pp. 2344-2348.
Borghi A. et al.: "Microbial De-Mannosylation and Mannosylation of Teicoplanin Derivatives" Journal of Antibiotics, Japan Antibiotics Research Association. Tokyo, JP, vol. 44, No. 12, Dec. 1991, pp. 1444-1451.
Malabarba A Nicas TI Ciabatti R: "Glycopeptide resistance in multiple antibiotic-resistant Gram-positive bacteria: a current challenge for novel semi-synthetic glycopeptide derivatives" European Journal of Medicinal Chemistry, Editions Scientifique Elsevier, Paris, FR, vol. 32, No. 6, Jun. 1, 1997, pp. 459-478.
Malabarba A. et al.: "Teicoplanin, Antibiotics from Actinoplanes Teichomyceticus Nov. SP. VII. Preparation and NMR Characteristics of the Aglycone of Teicoplanin" Journal of Antibiotics, Japan Antibiotics Research Association. Tokyo, JP, vol. 39, No. 10, Oct. 1986, pp. 1430-1442.

* cited by examiner

SEMI-SYNTHETIC GLYCOPEPTIDES WITH ANTIBIOTIC ACTIVITY

CROSS-REFERENCE TO RELATED APPLICATIONS

This application claims priority to U.S. Provisional Patent Application No. 60/657,297, filed Feb. 28, 2005, titled SEMI-SYNTHETIC GLYCOPEPTIDES WITH ANTIBIOTIC ACTIVITY, the disclosure of which is incorporated herein by reference in its entirety and for all purposes.

BACKGROUND OF THE INVENTION

1. Field of the Invention

This invention relates to novel semi-synthetic glycopeptides having antibacterial activity, to pharmaceutical compositions comprising these compounds, and to a medical method of treatment.

2. Description of Related Art

The emergence of drug resistant bacterial strains has highlighted the need for synthesizing and identifying antibiotics with improved activity. Naturally occurring and semi-synthetic glycopeptide antibiotics used to combat bacteria infections include compounds such as eremomycin (structure A, X═H), A82846B (structure A, X═Cl), vancomycin, teicoplanin, and A-40,926, having the scaffolds A, B, C and D, below respectively:

A

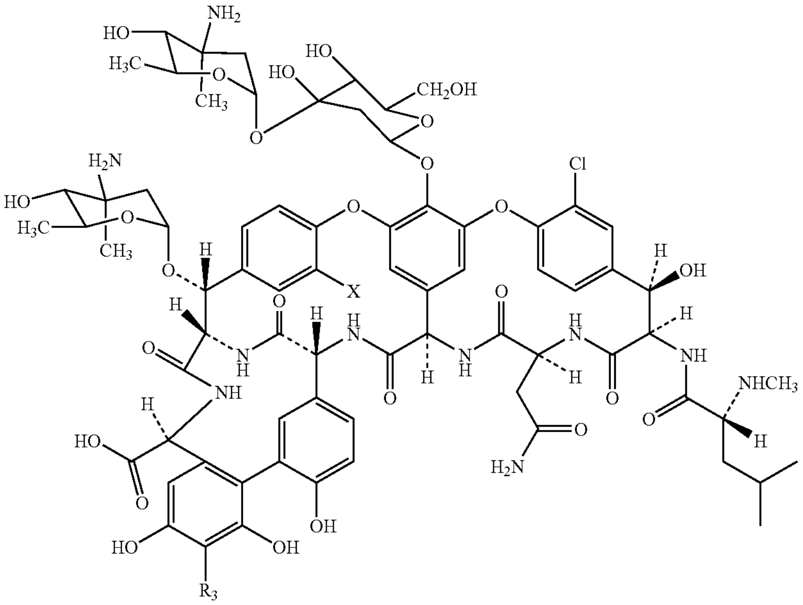

(X = H, Cl)

B

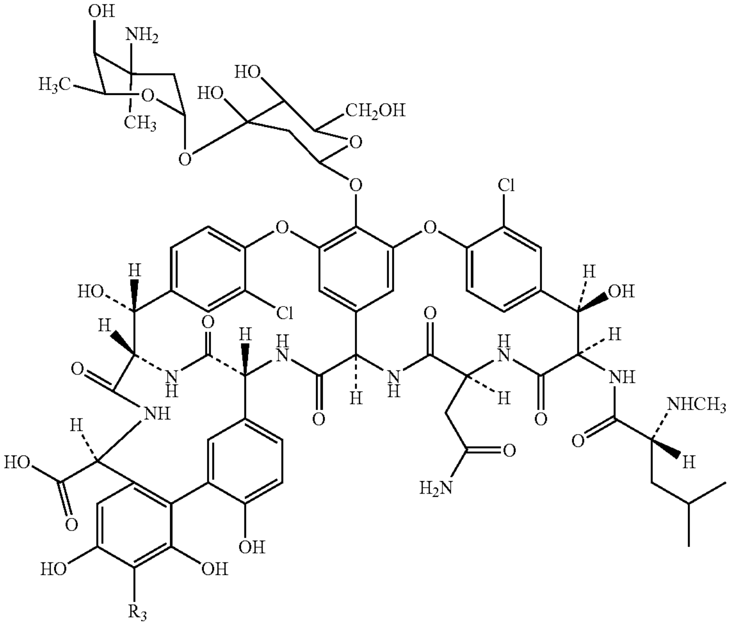

-continued

C

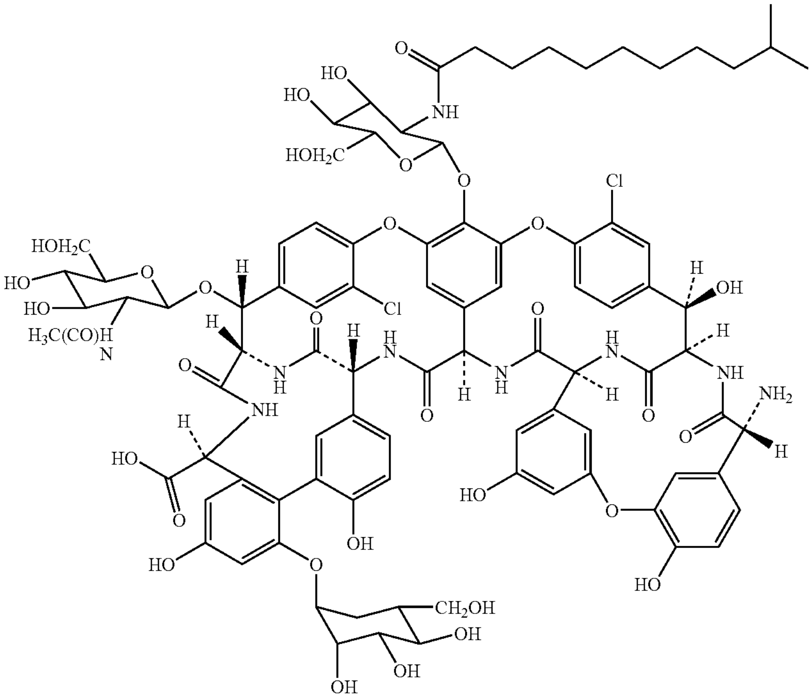

D

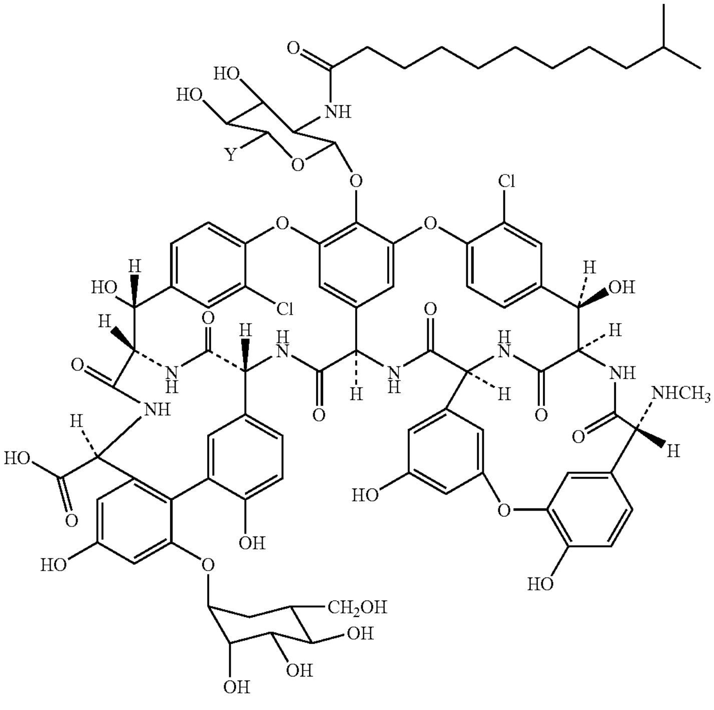

(Y = COOH, COOMe, $CH_2OH$)

These compounds are used to treat and prevent bacterial infection, but as with other antibacterial agents, bacterial strains having resistance or insufficient susceptibility to these compounds have been identified, and these compounds have been found to have limited effect against certain bacterial infections caused by glycopeptide resistant enterococci. Therefore, there is a continuing need to identify new derivative compounds which possess improved antibacterial activity, which have less potential for developing resistance, which possess improved effectiveness against bacterial infections that resist treatment with currently available antibiotics, or which possess unexpected selectivity against target microorganisms.

SUMMARY OF THE INVENTION

To achieve the foregoing, the present invention provides novel semi-synthetic glycopeptides that have antibacterial activity. The semi-synthetic glycopeptides of the invention are based on modifications of the eremomycin, A82846B, vancomycin, teicoplanin, and A-40,926 scaffolds, in particular, acylation of the amino substituent on the amino-substituted sugar moiety on these scaffolds with certain acyl groups, in particular amino acids or derivatives thereof; and/or conversion of the acid moiety on the macrocyclic ring of these scaffolds to certain substituted amides; or having a combination of an alkylation modification of the amino substituent on the amino-substituted sugar moiety on these scaffolds with certain alkyl groups or acylation modification of the amino substituent on the amino-substituted sugar moiety on this scaffold with certain alkyl groups, including β-amino acids or derivatives thereof, and conversion of the acid moiety on the macrocyclic ring of this scaffolds to certain substituted amides. Also provided are methods for synthesis of the compounds, pharmaceutical compositions containing the compounds, and methods of use of the compounds for the treatment and/or prophylaxis of diseases, especially bacterial infections.

In specific embodiments of the invention, the eremomycin, A82846B, vancomycin, teicoplanin, and A-40,926 scaffolds are modified to make a compound having a formula selected from the group consisting of:

1

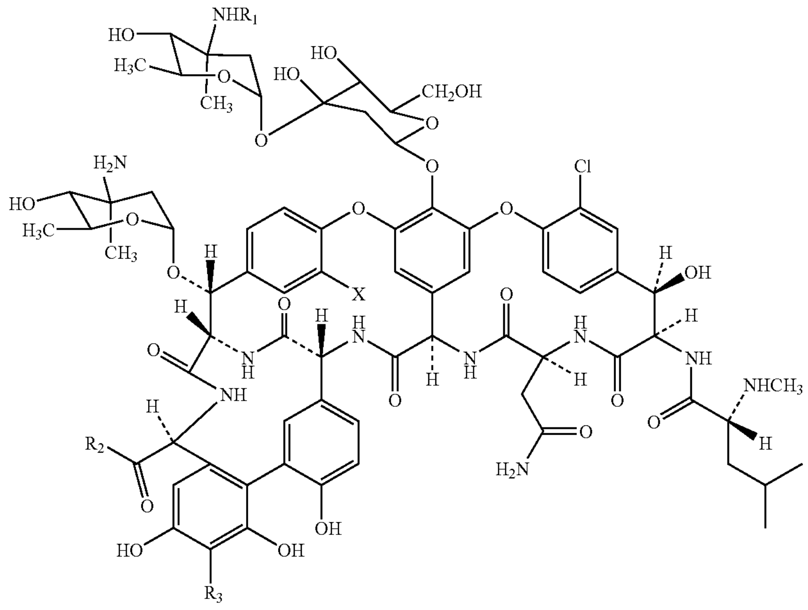

(X = H, Cl)

2

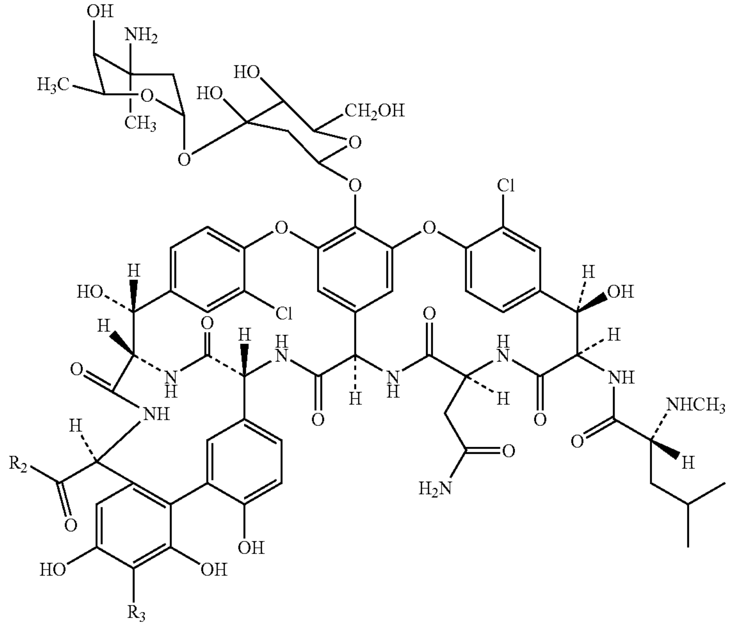

-continued
3
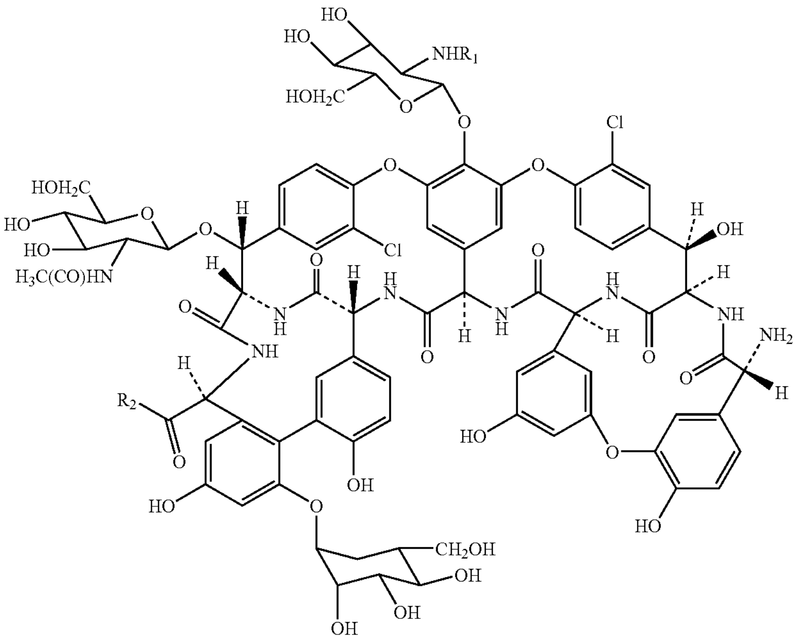
4
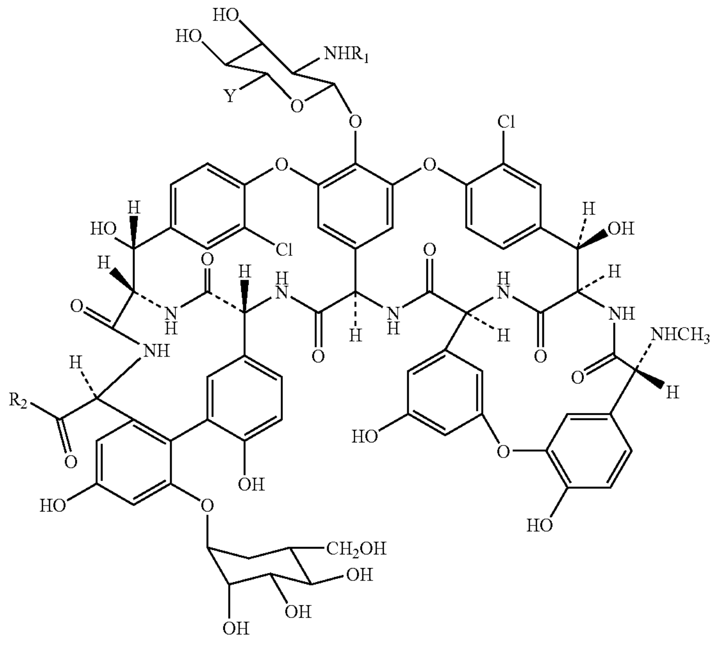
(Y = COOH, COOMe, $CH_2OH$)

-continued
1A
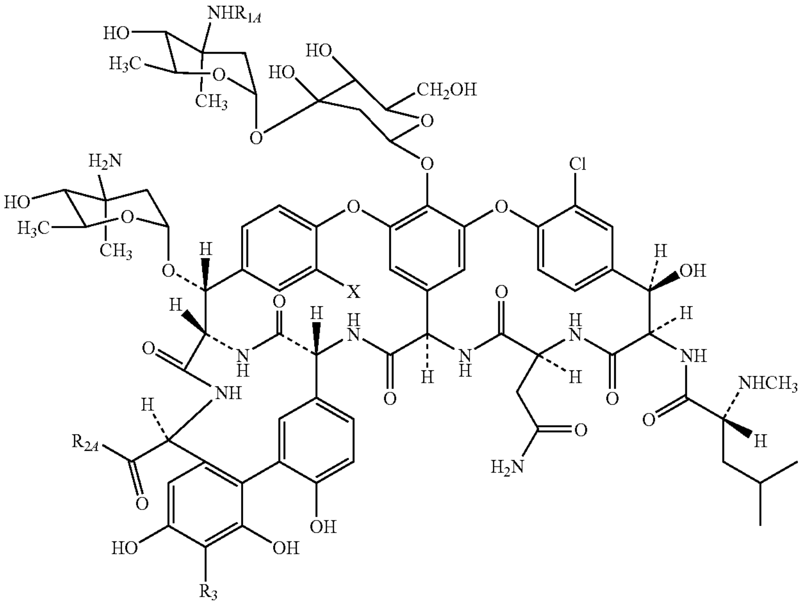
(X = H, Cl)
2A
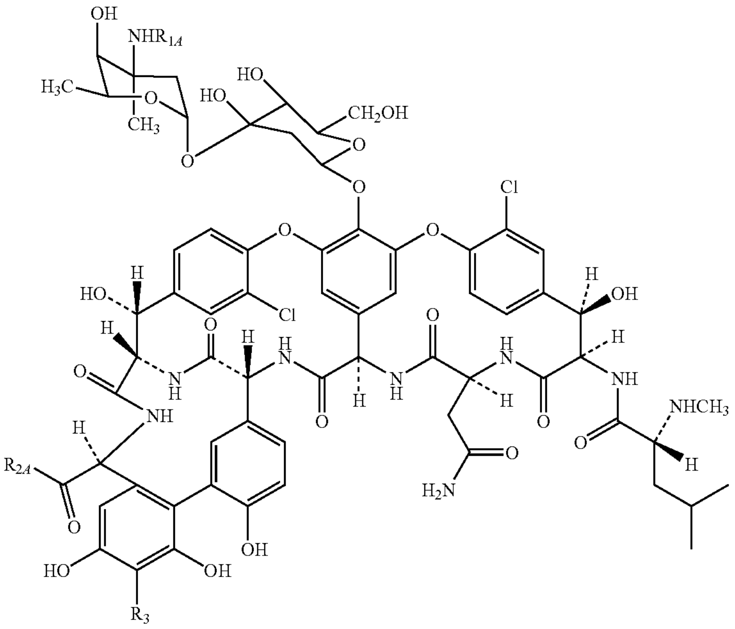

-continued

3A

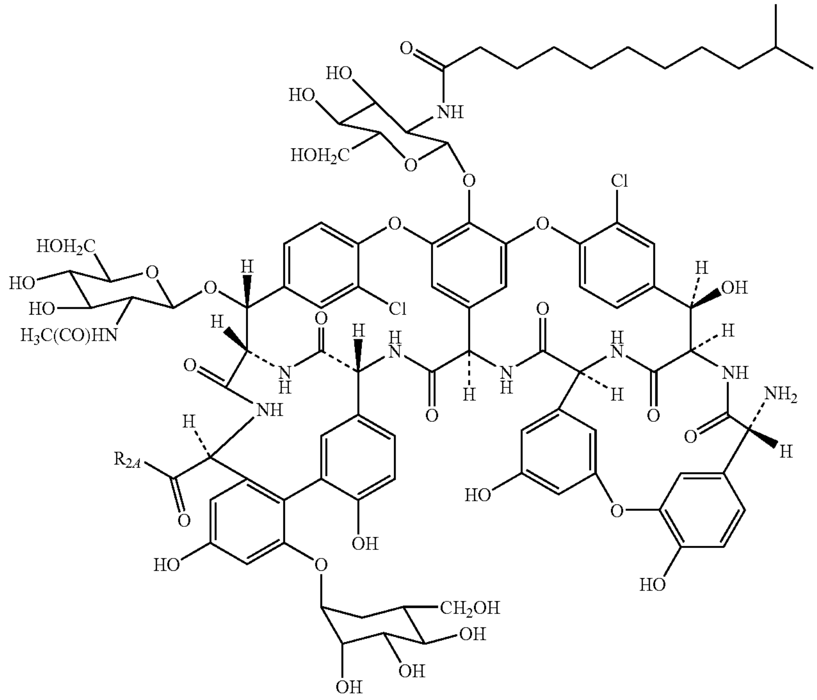

4A

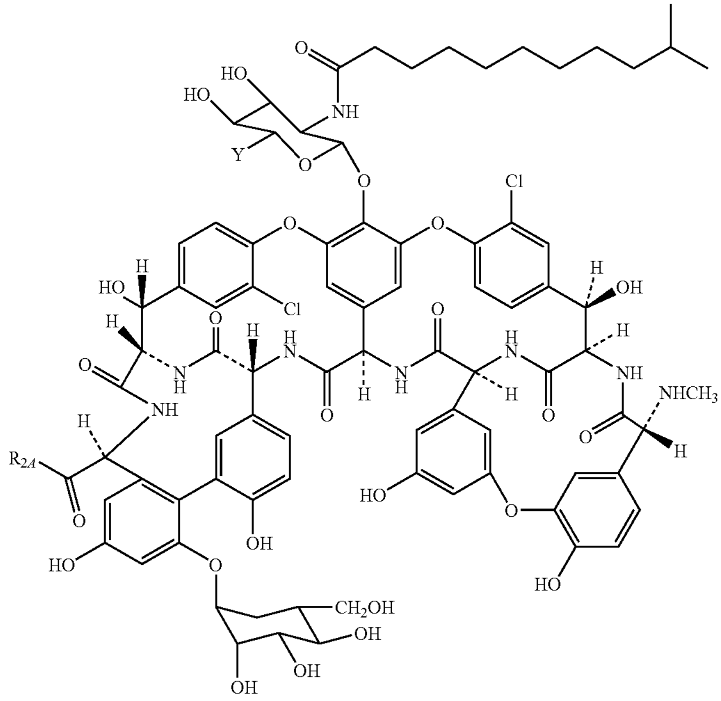

(Y = COOH, COOMe, $CH_2OH$)

wherein, $R_1$ is $C(=O)CR_7R_{7a}NR_8R_{8a}$, wherein, $R_7$ and $R_{7a}$ are independently hydrogen, the side chain of a naturally occurring or non-naturally occurring amino acid, alkyl, or alkyl substituted with one or more substituents selected from the group consisting of halogen, hydroxy, alkoxy, alkoxyalkoxy, carboxyl, carboxyl ester, —C(═O)$NR_8R_{8a}$, —$NR_8R_{8a}$, aryl, substituted aryl, heteroaryl, substituted heteroaryl, mercapto, or thioalkoxy, or $R_7$ and $R_{7a}$ together with the atom to which they are attached form a cycloalkyl ring which optionally contains a heteroatom selected from the group consisting of optionally substituted O, N, and S;

$R_8$ and $R_{8a}$ are independently selected from the group consisting of hydrogen and unsubstituted or substituted alkyl, alkenyl, cycloalkyl, cycloalkenyl, heterocycloalkyl, aryl, arylalkyl, alkylaryl, and heteroaryl, said aryl, alkylaryl, arylalkyl or heteroaryl group optionally containing one or more optionally substituted aryl, heteroaryl, or condensed rings, or $R_8$ and $R_{8a}$ together with the atom to which they are attached form a cycloalkyl ring which optionally contains a heteroatom selected from the group consisting of optionally substituted O, N, and S;

$R_{1A}$ is selected from the group consisting of H, $CHR_5R_{5a}$, and $C(=O)R_6$, wherein, $R_5$ and $R_{5a}$ are independently selected from the group consisting of hydrogen and unsubstituted or substituted alkyl, alkenyl, cycloalkyl, cycloalkenyl, heterocycloalkyl, aryl, arylalkyl, alkylaryl, and heteroaryl, said aryl, alkylaryl, arylalkyl or heteroaryl group optionally containing one or more optionally substituted aryl, heteroaryl, or condensed rings, or $R_5$ and $R_{5a}$ together with the atom to which they are attached form a cycloalkyl ring which optionally contains a heteroatom selected from the group consisting of optionally substituted O, N, and S, and $R_6$ is selected from the group consisting of unsubstituted or substituted alkyl, alkenyl, cycloalkyl, cycloalkenyl, heterocycloalkyl, aryl, arylalkyl, alkylaryl, and heteroaryl containing a heteroatom selected from the group consisting of optionally substituted O, N, and S, said aryl, alkylaryl, arylalkyl or heteroaryl group optionally containing one or more optionally substituted aryl, heteroaryl, or condensed rings;

$R_2$ is selected from the group consisting of, (1) OH,
(2) 1-adamantanamino,
(3) 2-adamantanamino,
(4) 3-amino-1-adamantanamino,
(5) 1-amino-3-adamantanamino,
(6) 3-loweralkylamino-1-adamantanamino,
(7) 1-loweralkylamino-3-adamantanamino,
(8) amino,
(9) $NR_9R_{9a}$ wherein $R_9$ and $R_{9a}$ are independently selected from the group consisting of hydrogen, loweralkyl or substituted loweralkyl, or $R_9$ and $R_{9a}$ together with the atom to which they are attached form a 3-10 membered heterocycloalkyl ring, which may optionally be substituted with one or more substituents independently selected from the group consisting of (a) halogen,
(b) hydroxy,
(c) $C_1$-$C_3$-alkoxy,
(d) $C_1$-$C_3$-alkoxy-$C_1$-$C_3$-alkoxy,
(e) oxo,
(f) $C_1$-$C_3$-alkyl,
(g) halo-$C_1$-$C_3$-alkyl, and
(h) $C_1$-$C_3$-alkoxy-$C_1$-$C_3$-alkyl;

$R_{2A}$ is selected from the group consisting of (1) 1-adamantanamino,
(2) 2-adamantanamino,
(3) 3-amino-1-adamantanamino,
(4) 1-amino-3-adamantanamino,
(5) 3-loweralkylamino-1-adamantanamino,
(6) 1-loweralkylamino-3-adamantanamino; and $R_3$ is selected from the group consisting of hydrogen and aminoloweralkyl, wherein the aminoloweralkyl amino group is further substituted with unsubstituted or substituted alkyl, alkenyl, cycloalkyl, cycloalkenyl, aryl, arylalkyl, alkylaryl, alkoxy, aryloxy, substituted alkoxy, and substituted aryloxy;

or a pharmaceutically acceptable salt, ester, solvate, stereoisomer, tautomer or prodrug thereof.

The present invention also provides pharmaceutical compositions which comprise a therapeutically effective amount of a compound as defined above in combination with a pharmaceutically acceptable carrier.

The invention further relates to methods of treating bacterial infections in a host mammal in need of such treatment comprising administering to a mammal in need of such treatment a therapeutically effective amount of a compound of the invention as defined above.

In a further aspect of the present invention are provided processes for the preparation of semi-synthetic glycopeptides defined above.

DESCRIPTION OF SPECIFIC EMBODIMENTS OF THE INVENTION

The materials and associated techniques and apparatuses of the present invention will now be described with reference to several embodiments. Important properties and characteristics of the described embodiments are illustrated in the structures in the text. While the invention will be described in conjunction with these embodiments, it should be understood that the invention it is not intended to be limited to these embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Introduction

The present invention provides novel semi-synthetic glycopeptides that have antibacterial activity. The semi-synthetic glycopeptides of the invention are based on modifications of the eremomycin, A82846B, vancomycin, teicoplanin, and A-40,926 scaffolds, in particular, acylation of the amino substituent on the amino-substituted sugar moiety on these scaffolds with certain acyl groups; and conversion of the acid moiety on the macrocyclic ring of these scaffolds to certain substituted amides. Also provided are methods for synthesis of the compounds, pharmaceutical compositions containing the compounds, and methods of use of the compounds for the treatment and/or prophylaxis of diseases, especially bacterial infections.

Compounds of the Invention

In specific embodiments of the invention, the eremomycin, A82846B, vancomycin, teicoplanin, and A-40,926 scaffolds are modified to make a compound having a formula selected from the group consisting of:

1
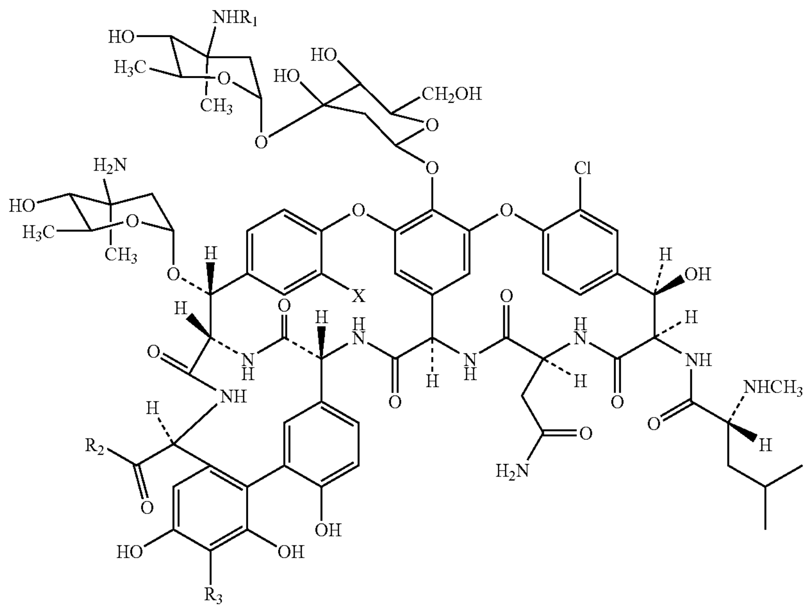
(X = H, Cl)
2
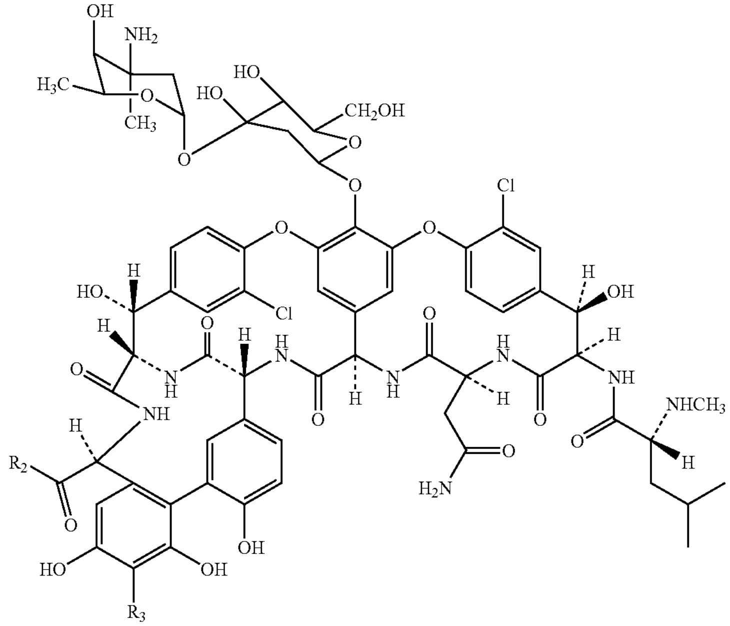

-continued
3
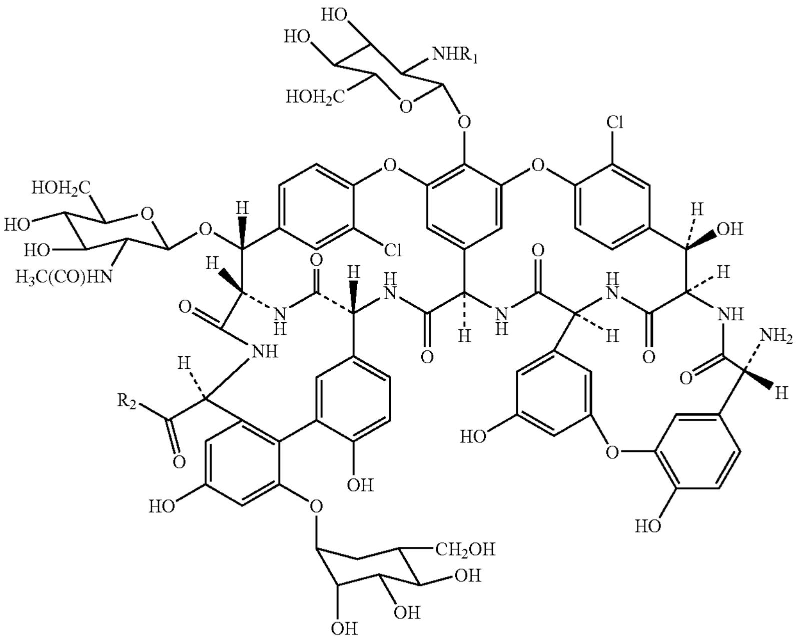
4
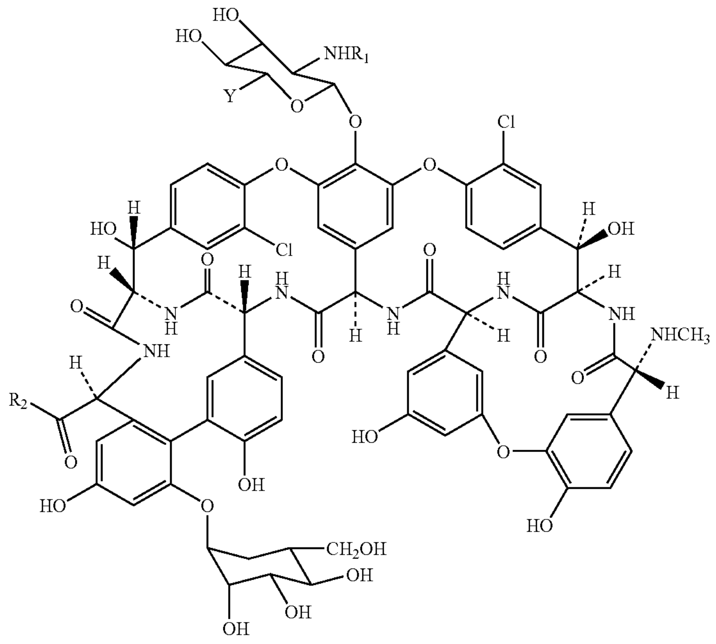
(Y = COOH, COOMe, $CH_2OH$)

-continued
1A
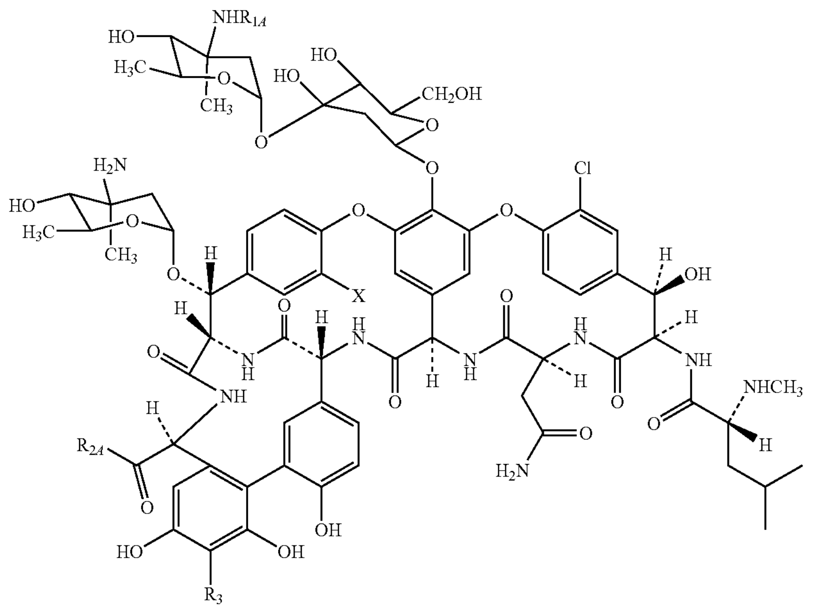
(X = H, Cl)
2A
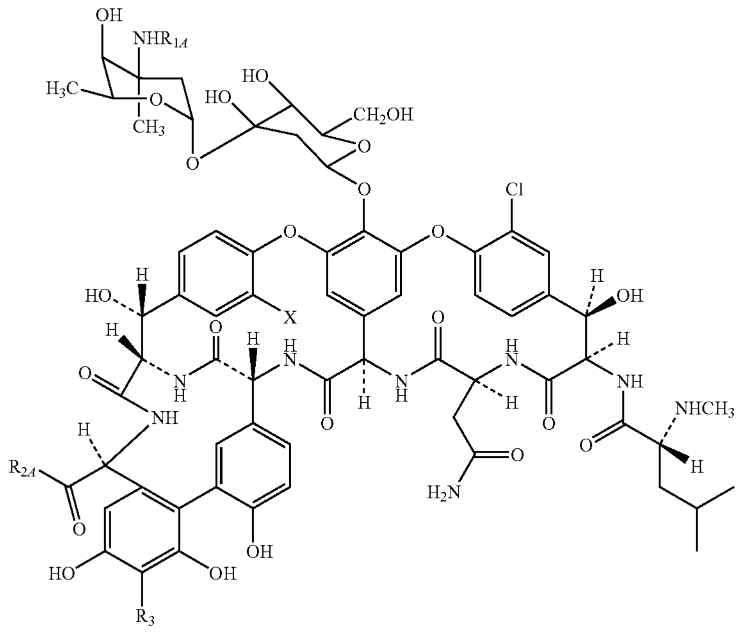

-continued

3A

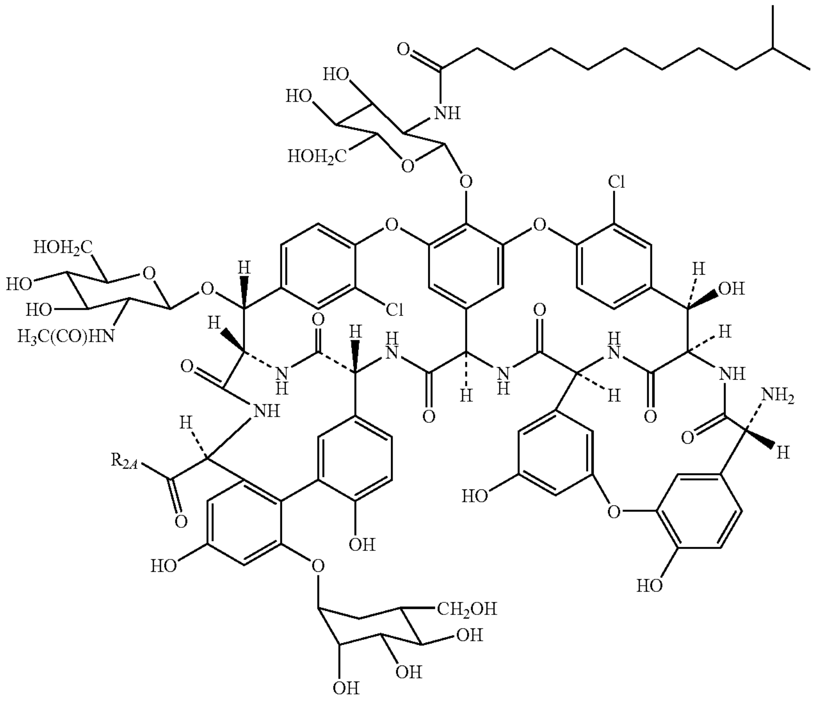

4A

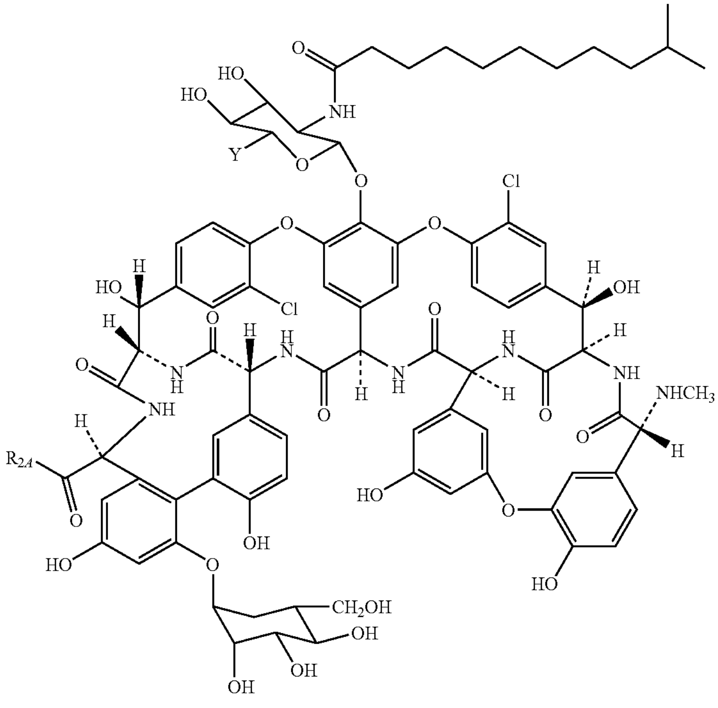

(Y = COOH, COOMe, $CH_2OH$)

wherein, $R_1$ is $C(=O)CR_7R_{7a}NR_8R_{8a}$, wherein, $R_7$ and $R_{7a}$ are independently hydrogen, the side chain of a naturally occurring or non-naturally occurring amino acid, alkyl, or alkyl substituted with one or more substituents selected from the group consisting of halogen, hydroxy, alkoxy, alkoxyalkoxy, carboxyl, carboxyl ester, $—C(=O)NR_8R_{8a}$, $—NR_8R_{8a}$, aryl, substituted aryl, heteroaryl, substituted heteroaryl, mercapto, or thioalkoxy, or $R_7$ and $R_{7a}$ together with the atom to which they are attached form a cycloalkyl ring which optionally contains a heteroatom selected from the group consisting of optionally substituted O, N, and S;

$R_8$ and $R_{8a}$ are independently selected from the group consisting of hydrogen and unsubstituted or substituted alkyl, alkenyl, cycloalkyl, cycloalkenyl, heterocycloalkyl, aryl, arylalkyl, alkylaryl, and heteroaryl, said aryl, alkylaryl, arylalkyl or heteroaryl group optionally containing one or more optionally substituted aryl, heteroaryl, or condensed rings, or $R_8$ and $R_{8a}$ together with the atom to which they are attached form a cycloalkyl ring which optionally contains a heteroatom selected from the group consisting of optionally substituted O, N, and S;

$R_{1A}$ is selected from the group consisting of H, $CHR_5R_{5a}$, and $C(=O)R_6$, wherein, $R_5$ and $R_{5a}$ are independently selected from the group consisting of hydrogen and unsubstituted or substituted alkyl, alkenyl, cycloalkyl, cycloalkenyl, heterocycloalkyl, aryl, arylalkyl, alkylaryl, and heteroaryl, said aryl, alkylaryl, arylalkyl or heteroaryl group optionally containing one or more optionally substituted aryl, heteroaryl, or condensed rings, or $R_5$ and $R_{5a}$ together with the atom to which they are attached form a cycloalkyl ring which optionally contains a heteroatom selected from the group consisting of optionally substituted O, N, and S, and $R_6$ is selected from the group consisting of unsubstituted or substituted alkyl, alkenyl, cycloalkyl, cycloalkenyl, heterocycloalkyl, aryl, arylalkyl, alkylaryl, and heteroaryl said aryl, alkylaryl, arylalkyl or heteroaryl group optionally containing one or more optionally substituted aryl, heteroaryl, or condensed rings;

$R_2$ is selected from the group consisting of, (1) OH,
(2) 1-adamantanamino,
(3) 2-adamantanamino,
(4) 3-amino-1-adamantanamino,
(5) 1-amino-3-adamantanamino,
(6) 3-loweralkylamino-1-adamantanamino,
(7) 1-loweralkylamino-3-adamantanamino,
(8) amino,
(9) $NR_9R_{9a}$ wherein $R_9$ and $R_{9a}$ are independently selected from the group consisting of hydrogen, loweralkyl or substituted loweralkyl, or $R_9$ and $R_{9a}$ together with the atom to which they are attached form a 3-10 membered heterocycloalkyl ring, which may optionally be substituted with one or more substituents independently selected from the group consisting of (a) halogen,
(b) hydroxy,
(c) $C_1$-$C_3$-alkoxy,
(d) $C_1$-$C_3$-alkoxy-$C_1$-$C_3$-alkoxy,
(e) oxo,
(f) $C_1$-$C_3$-alkyl,
(g) halo-$C_1$-$C_3$-alkyl, and
(h) $C_1$-$C_3$-alkoxy-$C_1$-$C_3$-alkyl;

$R_{2A}$ is selected from the group consisting of (1) 1-adamantanamino,
(2) 2-adamantanamino,
(3) 3-amino-1-adamantanamino,
(4) 1-amino-3-adamantanamino,
(5) 3-loweralkylamino-1-adamantanamino,
(6) 1-loweralkylamino-3-adamantanamino; and $R_3$ is selected from the group consisting of hydrogen and aminoloweralkyl, wherein the aminoloweralkyl amino group is further substituted with unsubstituted or substituted alkyl, alkenyl, cycloalkyl, cycloalkenyl, aryl, arylalkyl, alkylaryl, alkoxy, aryloxy, substituted alkoxy, and substituted aryloxy;

or a pharmaceutically acceptable salt, ester, solvate, stereoisomer, tautomer or prodrug thereof.

According to specific embodiments of the invention, the various substituents may be as follows:

Within $R_{1A}$:

$R_5$ may be hydrogen and $R_{5a}$ may be selected from the group consisting of unsubstituted or substituted alkyl, alkenyl, cycloalkyl, cycloalkenyl, heterocycloalkyl, aryl, arylalkyl, alkylaryl, and heteroaryl, said aryl, alkylaryl, arylalkyl or heteroaryl group optionally containing one or more optionally substituted aryl, heteroaryl, or condensed rings, or $R_5$ and $R_{5a}$ together with the atom to which they are attached form a cycloalkyl ring which optionally contains a heteroatom selected from the group consisting of optionally substituted O, N, and S.

$R_6$ may be β-amino acid analog. Such a group will include a $-CH_2CHNH-$portion. For example, $R_6$ may be $CH_2C(R_7)(R_{7a})(NR_8R_{8a})$ wherein $R_7$, $R_{7a}$, $R_8$, and $R_{8a}$ are previously defined or $-CR_7R_{7a}$ together with $NR_8R_{8a}$ form a pyrrolidine ring.

Within $R_1$, the $C(=O)CR_7R_{7a}NR_8R_{8a}$ may be an amino acid moiety, such that $R_7$, $R_8$ and $R_{8a}$ are each H and $R_{7a}$ is one of H, $CH_3$, $CH(CH_3)_2$, $CH_2CH(CH_3)_2$, $CH(CH_3)CH_2CH_3$, $(CH_2)_4NH_2$, $CH_2OH$, $CH(OH)CH_3$, $CH_2COOH$, $(CH_2)_2COOH$, $CH_2C(=O)NH_2$, $(CH_2)_2C(=O)NH_2$, $CH_2SH$, $(CH_2)_2SCH_3$, $(CH_2)_3NHC(=NH)NH_2$, $CH_2C_6H_5$, $CH_2C_6H_4OH$, $CH_2$(4-imidazoyl) or $CH_2$(3-indolyl), or $-CR_7R_{7a}$ together with $NR_8R_{8a}$ form a pyrrolidine ring.

Alternatively, $R_7$ may be H and $R_{7a}$ may be selected from the group consisting of (1) hydrogen,
(2) $C_1$-$C_{12}$-alkyl, and
(3) $C_1$-$C_{12}$-alkyl substituted with one or more substituents selected from the group consisting of (a) halogen,
(b) hydroxy,
(c) $C_1$-$C_3$-alkoxy,
(d) $C_1$-$C_3$-alkoxy-$C_1$-$C_3$-alkoxy,
(e) $-CO_2R_5$ wherein $R_5$ is hydrogen, loweralkyl or substituted loweralkyl,
(f) $-C(=O)NR_9R_{9a}$,
(g) amino, and
(h)$-NR_9R_{9a}$, or $R_9$ and $R_{9a}$ together with the atom to which they are attached form a 3-10 membered heterocycloalkyl ring optionally substituted with one or more substituents independently selected from the group consisting of (i) halogen.
(ii) hydroxy,
(iii) $C_1$-$C_3$-alkoxy,
(iv) $C_1$-$C_3$-alkoxy-$C_1$-$C_3$-alkoxy,
(v) oxo,
(vi) $C_1$-$C_3$-alkyl,
(vii) halo-$C_1$-$C_3$-alkyl, and
(viii) $C_1$-$C_3$-alkoxy-$C_1$-$C_3$-alkyl, (i) aryl,
(j) substituted aryl,
(k) heteroaryl,
(l) substituted heteroaryl,
(m) mercapto, and
(n) $C_1$-$C_3$-thioalkoxy.

In addition, $R_8$ and $R_{8a}$ may be independently selected from the group consisting of, (1) hydrogen,
(2) $C_1$-$C_{12}$-alkyl,
(3) $C_2$-$C_{12}$-alkyl substituted with one or more substituents selected from the group consisting of (a) halogen,
(b) hydroxy, (c) $C_1$-$C_3$-alkoxy, (d) $C_1$-$C_3$-alkoxy-$C_1$-$C_3$-alkoxy, (e) amino, and (f) $C_1$-$C_3$-alkylamino, (4) $C_1$-$C_{12}$-alkyl substituted with aryl, (5) $C_1$-$C_{12}$-alkyl substituted with substituted aryl, (6) $C_1$-$C_{12}$-alkyl substituted with heteroaryl, and (7) $C_1$-$C_{12}$-alkyl substituted with substituted heteroaryl; or $R_8$ and $R_{8a}$ together with the atom to which they are attached form a $C_3$-$C_7$-heterocycloalkyl ring which, when the ring is a 5- to 7-membered ring, optionally contains a hetero function selected from the group consisting of —O—, —NH, —N($C_1$-$C_6$-alkyl-)-, —N(aryl)-, —N(aryl-$C_1$-$C_6$-alkyl-)-, —N (substituted-aryl-$C_1$-$C_6$-alkyl-)-, —N(heteroaryl)-, —N(heteroaryl-$C_1$-$C_6$-alkyl-)-, —N(substituted-heteroaryl-$C_1$-$C_6$-alkyl-)-, and —S— or S(=O)$_n$— wherein n is 1 or 2.

In a specific embodiment, the compound may be one of N'-p-BuBnHNCH$_2$CO eremomycin, N'-stilbenylHNCH$_2$CO eremomycin, N'-p-$C_8H_{17}$OBnHNCH$_2$CO vancomycin, N'-p-$C_6H_{17}$OBnHNCH($CH_3$)CO vancomycin and 2-adamantanamino eremomycin.

Definitions

Unless otherwise noted, terminology used herein should be given its normal meaning as understood by one of skill in the art. In order to facilitate understanding of the present invention, a number of defined terms are used herein to designate particular elements of the present invention. When so used, the following meanings are intended:

The term "alkyl" as used herein refers to saturated, straight- or branched-chain hydrocarbon radicals derived from a hydrocarbon moiety containing between one and twenty carbon atoms by removal of a single hydrogen atom.

The term "alkenyl" as used herein refers to unsaturated, straight- or branched-chain hydrocarbon radicals derived from a hydrocarbon moiety containing between two and twenty carbon atoms by removal of a single hydrogen atom.

The term "cycloalkyl" as used herein refers to a monovalent group derived from a monocyclic or bicyclic saturated carbocyclic ring compound containing between three and twenty carbon atoms by removal of a single hydrogen atom.

The term "cycloalkenyl" as used herein refers to a monovalent group derived from a monocyclic or bicyclic unsaturated carbocyclic ring compound containing between three and twenty carbon atoms by removal of a single hydrogen atom.

The terms "$C_1$-$C_3$-alkyl", "$C_1$-$C_6$-alkyl", and "$C_1$-$C_{12}$-alkyl" as used herein refer to saturated, straight- or branched-chain hydrocarbon radicals derived from a hydrocarbon moiety containing between one and three, one and six, and one and twelve carbon atoms, respectively, by removal of a single hydrogen atom. Examples of $C_1$-$C_3$-alkyl radicals include methyl, ethyl, propyl and isopropyl. Examples of $C_1$-$C_6$-alkyl radicals include, but not limited to, methyl, ethyl, propyl, isopropyl, n-butyl, tert-butyl, neopentyl and n-hexyl. Examples of $C_1$-$C_{12}$-alkyl radicals include, but not limited to, methyl, ethyl, propyl, isopropyl, n-butyl, tert-butyl, neopentyl, n-hexyl, n-heptyl, n-octyl, n-nonyl, n-decyl, n-undecyl and n-docecyl.

The term substituted loweralkyl as used herein refers to $C_1$-$C_{12}$-alkyl substituted by one, two or three groups consisting of halogen, alkoxy, amino, alkylamino, dialkylamino, hydroxy, aryl, heteroaryl, alkene or alkyne groups.

The term "$C_3$-$C_{12}$-cycloalkyl" denotes a monovalent group derived from a monocyclic or bicyclic saturated carbocyclic ring compound by removal of a single hydrogen atom. Examples include cyclopropyl, cyclobutyl, cyclopentyl, cyclohexyl, bicyclo[2.2.1]heptyl, and bicyclo[2.2.2]octyl.

The terms "$C_1$-$C_3$-alkoxy", "$C_1$-$C_6$-alkoxy" as used herein refers to the $C_1$-$C_3$-alkyl group and $C_1$-$C_6$-alkyl group, as previously defined, attached to the parent molecular moiety through an oxygen atom. Examples of $C_1$-$C_6$-alkoxy radicals include, but not limited to, methoxy, ethoxy, propoxy, isopropoxy, n-butoxy, tert-butoxy, neopentoxyl and n-hexoxy.

The term "oxo" denotes a group wherein two hydrogen atoms on a single carbon atom in an alkyl group as defined above are replaced with a single oxygen atom (i.e., a carbonyl group).

The term "aryl" as used herein refers to a mono- or bicyclic carbocylic ring system having one or two aromatic rings including, but not limited to, phenyl, naphthyl, tetrahydronaphthyl, indanyl, indenyl and the like and can be unsubstituted or substituted (including bicyclic aryl groups) with one, two or three substituents independently selected from loweralkyl, substituted loweralkyl, haloalkyl, $C_1$-$C_{12}$-alkoxy, thioalkoxy, $C_1$-$C_{12}$-thioalkoxy, aryloxy, amino, alkylamino, dialkylamino, acylamino, cyano, hydroxy, halogen, mercapto, nitro, carboxaldehyde, carboxy, alkoxycarbonyl and carboxamide. In addition, substituted aryl groups include tetrafluorophenyl and pentafluorophenyl.

The term "arylalkyl" as used herein refers to an aryl group as defined above attached to the parent molecular moiety through an alkyl group wherein the alkyl group is of one to twelve carbon atoms.

The term "alkylaryl" as used herein refers to an alky group as defined above attached to the parent molecular moiety through an aryl group.

The term "halo" and "halogen" as used herein refer to an atom selected from fluorine, chlorine, bromine and iodine.

The term "alkylamino" refers to a group having the structure —NHR' wherein R' is alkyl, as previously defined. Examples of alkylamino include methylamino, ethylamino, iso-propylamino, and the like.

The term "loweralkylamino" as used herein refers to $C_1$-$C_6$-alkyl groups, as previously defined, attached to the parent molecular moiety through a nitrogen atom. Examples of $C_1$-$C_3$-alkylamino include, but are not limited to methylamino, dimethylamino, ethylamino, diethylamino, and propylamino.

The term "dialkylamino" refers to a group having the structure —NHR'R" wherein R' and R" are independently selected from alkyl, as previously defined. Additionally, R' and R" taken together may optionally be —$(CH_2)_k$— where k is an integer of from 2 to 6. Examples of dialkylamino include dimethylamino, diethylamino, methylpropylamino, piperidino, and the like.

The term "haloalkyl" denotes an alkyl group, as defined above, having one, two or three halogen atoms attached thereto and is exemplified by such group as chloromethyl, bromoethyl, trifluoromethyl, and the like.

The term "alkoxycarbonyl" represents as ester group; i.e. an alkoxy group, attached to the parent molecular moiety through a carbonyl group such as methoxycarbonyl, ethoxycarbonyl, and the like.

The term "thioalkoxy" refers to an alkyl group previously defined attached to the parent molecular moiety through a sulfur atom.

The term "carboxaldehyde" as used herein refers to a group of formula —CHO.

The term "carboxy" as used herein refers to a group of formula —$CO_2$H.

The term "carboxamide" as used herein refers to a group of formula —CONHR'R" wherein R' and R" are independently selected from hydrogen, alkyl, or R' and R" taken together may optionally be —$(CH_2)_k$— where k is an integer of from 2 to 6.

The term "heteroaryl", as used herein, refers to a cyclic or bicyclic aromatic radical having from five to ten ring atoms in each ring of which at least one atom of the cyclic or bicyclic ring is selected from optionally substituted S, O, and N; zero, one or two ring atoms are additional heteroatoms independently selected from optionally substituted S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, naphthyridinyl; and the like.

The term "heterocycloalkyl" as used herein, refers to a non-aromatic partially unsaturated or fully saturated 3- to 10-membered ring system, which includes single rings of 3 to 8 atoms in size and bi- or tri-cyclic ring systems which may include aromatic six-membered aryl or heteroaryl rings fused to a non-aromatic ring. These heterocycloalkyl rings include those having from one to three heteroatoms independently selected from oxygen, sulfur and nitrogen, in which the nitrogen and sulfur heteroatoms may optionally be oxidized and the nitrogen heteroatom may optionally be quaternized. Representative heterocycloalkyl rings include, but not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "heteroarylalkyl" as used herein, refers to a heteroaryl group as defined above attached to the parent molecular moiety through an alkyl group wherein the alkyl group is of one to twelve carbon atoms.

"Protecting group" refers to an easily removable group which is known in the art to protect a functional group, for example, a hydroxyl, ketone or amine, against undesirable reaction during synthetic procedures and to be selectively removable. The use of protecting groups is well known in the art for protecting groups against undesirable reaction during synthetic procedure and many such protecting groups are known, cf., for example, T. H. Greene and P. G. M. Wuts, *Protective Groups in Organic Synthesis,* 2nd edition, John Wiley & Sons, New York (1991). Examples of hydroxy-protecting groups include, but are not limited to, methylthiomethyl, tert-dimethylsilyl, tert-butyldiphenylsilyl, ethers such as methoxymethyl, and esters including acetyl, benzoyl, and the like. Examples of ketone protecting groups include, but are not limited to, ketals, oximes, O-substituted oximes for example O-benzyl oxime, O-phenylthiomethyl oxime, 1-isopropoxycyclohexyl oxime, and the like. Examples of amine protecting groups include, but are not limited to, tert-butoxycarbonyl (Boc) and carbobenzyloxy (Cbz).

The term "amino acid" refers to amino acids having D or L stereochemistry, and also refers to synthetic, non-natural amino acids having side chains other than those found in the 20 common amino acids. Non-natural amino acids are commercially available or may be prepared according to U.S. Pat. No. 5,488,131 and references therein. Amino acids may be further substituted to contain modifications to their amino, carboxy, or side chain groups. These modifications include the numerous protecting groups commonly used in peptide synthesis (T. H. Greene and P. G. M. Wuts, *Protective Groups in Organic Synthesis,* 2nd edition, John Wiley & Sons, New York, 1991).

The term "substituted aryl" as used herein, refers to an aryl group as defined herein substituted by independent replacement of one, two or three of the hydrogen atoms thereon with Cl, Br, F, I, OH, CN, $C_1$-$C_{12}$-alkyl, $C_1$-$C_{12}$-alkoxy, $C_1$-$C_{12}$-alkoxy substituted with aryl, C1-C12-alkoxy substituted with substituted aryl, haloalkyl, thioalkyl, amino, alkylamino, dialkylamino, mercapto, nitro, carboxaldehyde, carboxy, alkoxycarbonyl and carboxamide. In addition, any one substituent may be an aryl, heteroaryl, or hetercycloalkyl group.

The term "substituted heteroaryl" as used herein, refers to a heteroaryl group as defined herein substituted by independent replacement of one, two or three of the hydrogen atoms thereon with Cl, Br, F, I, OH, CN, $C_1$-$C_{12}$-alkyl, $C_1$-$C_{12}$-alkoxy, $C_1$-$C_{12}$-alkoxy substituted with aryl, haloalkyl, thioalkyl, amino, alkylamino, dialkylamino, mercapto, nitro, carboxaldehyde, carboxy, alkoxycarbonyl and carboxamide. In addition, any one substituent may be an aryl, heteroaryl, or hetercycloalkyl group.

The term "substituted heterocycloalkyl" as used herein, refers to a heterocycloalkyl group as defined herein substituted by independent replacement of one, two or three of the hydrogen atoms thereon with Cl, Br, F, I, OH, CN, $C_1$-$C_{12}$-alkyl, $C_1$-$C_{12}$-alkoxy, $C_1$-$C_{12}$-alkoxy substituted with aryl, haloalkyl, thioalkyl, amino, alkylamino, dialkylamino, mercapto, nitro, carboxaldehyde, carboxy, alkoxycarbonyl and carboxamide. In addition, any one substituent may be an aryl, heteroaryl, or hetercycloalkyl group.

The term "adamantanamino" as used herein, refers to a fully saturated tricyclo [3.3.1.1(3,7)] 10-membered carbon ring system with one or more amino substituents. Examples include 1-adamantanamino, 2-adamantanamino, 3-amino-1-adamantanamino, 1-amino-3-adamantanamino, 3-lower-alkylamino-1-adamantanamino, and 1-loweralkylamino-3-adamantanamino.

The term "stereoisomer" as used herein, refers to either of two forms of a compound having the same molecular formula and having their constituent atoms attached in the same order, but having different arrangement of their atoms in space about an asymmetric center. Numerous asymmetric centers may exist in the compounds of the present invention. Except where otherwise noted, the present invention contemplates the various stereoisomers and mixtures thereof. Accordingly, except where otherwise noted, it is intended that a mixture of stereo-orientations or an individual isomer of assigned or unassigned orientation may be present.

The term "tautomer" as used herein refers to either of the two forms of a chemical compound that exhibits tautomerism, which is the ability of certain chemical compounds to exist as a mixture of two interconvertible isomers in equilibrium via hydrogen transfer. The keto and enol forms of carbonyl compounds are examples of tautomers. They are interconvertible in the presence of traces of acids and bases via a resonance stabilized anion, the enolate ion.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 66: 1-19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower-alkyl sulfonate and aryl sulfonate.

The term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

The term "solvate" as used herein refers to a compound formed by salvation, the combination of solvent molecules with molecules or ions of solute composed of a compound according to the present invention. The term "pharmaceutically acceptable solvate" refers to those solvates which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable solvates are well known in the art.

The term "pharmaceutically acceptable prodrugs" refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

Synthetic Methods

Synthesis of the compounds of the invention can be broadly summarized as follows. The compounds of the invention may be made by coupling functionalized or unfunctionalized glycopeptides with the appropriate acyl, alkyl and/or amino groups under amide formation conditions. In particular, the semi-synthetic glycopeptides of the invention are made by modifying an eremomycin, A82846B, vancomycin, teicoplanin or A-40,926 scaffold, in particular, by acylation of the amino substituent on the amino-substituted sugar moiety on this scaffold with certain acyl groups, in particular amino acids or derivatives thereof; and/or conversion of the acid moiety on the macrocyclic ring of this scaffolds to certain substituted amides; or having a combination of an alkylation modification of the amino substituent on the amino-substituted sugar moiety on this scaffold with certain alkyl groups or acylation modification of the amino substituent on the amino-substituted sugar moiety on this scaffold with certain alkyl groups, including β-amino acids or derivatives thereof, and conversion of the acid moiety on the macrocyclic ring of this scaffolds to certain substituted amides.

In particular, the semi-synthetic glycopeptides of the invention may be made by modifying one of an eremomycin, A82846B, vancomycin, teicoplanin or A-40,926 scaffold,

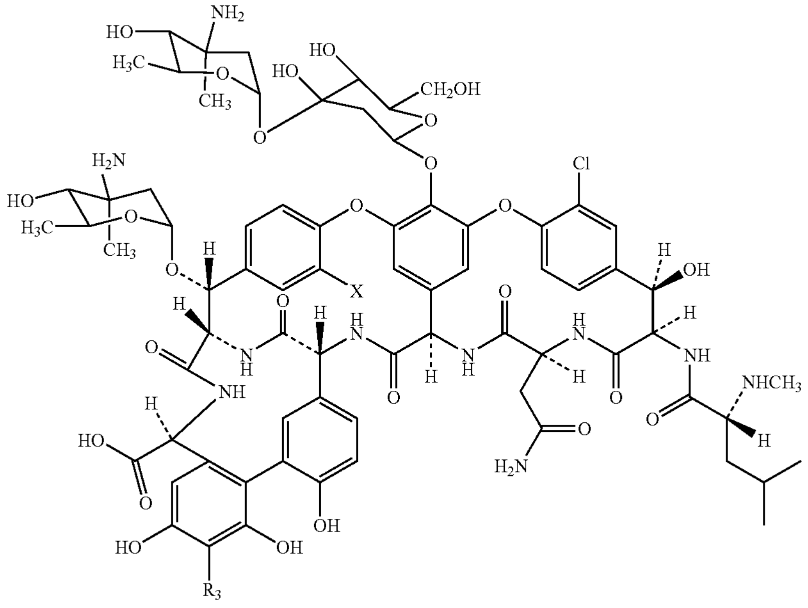

(X = H, Cl)

-continued
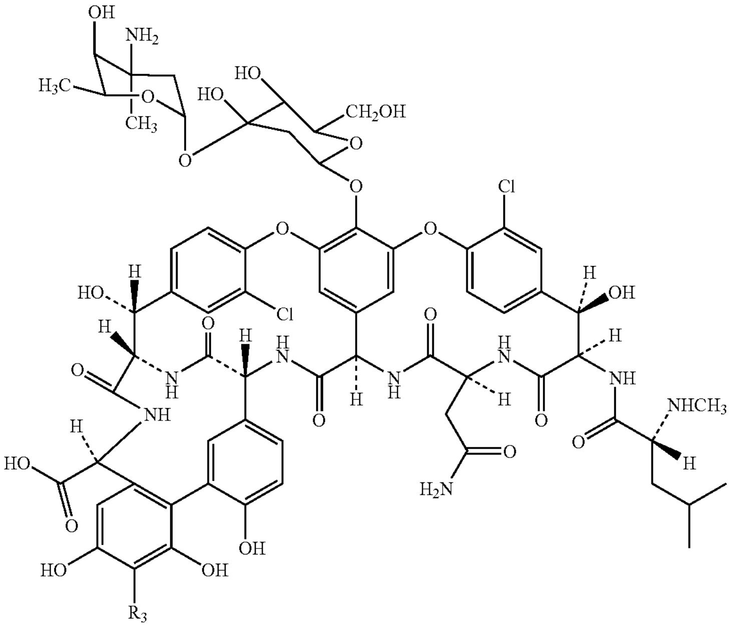
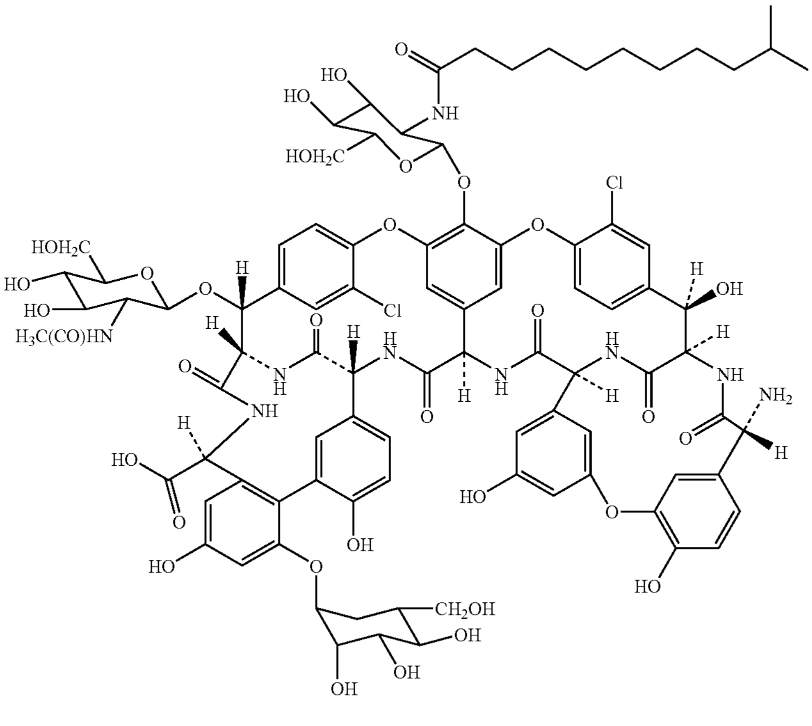

-continued

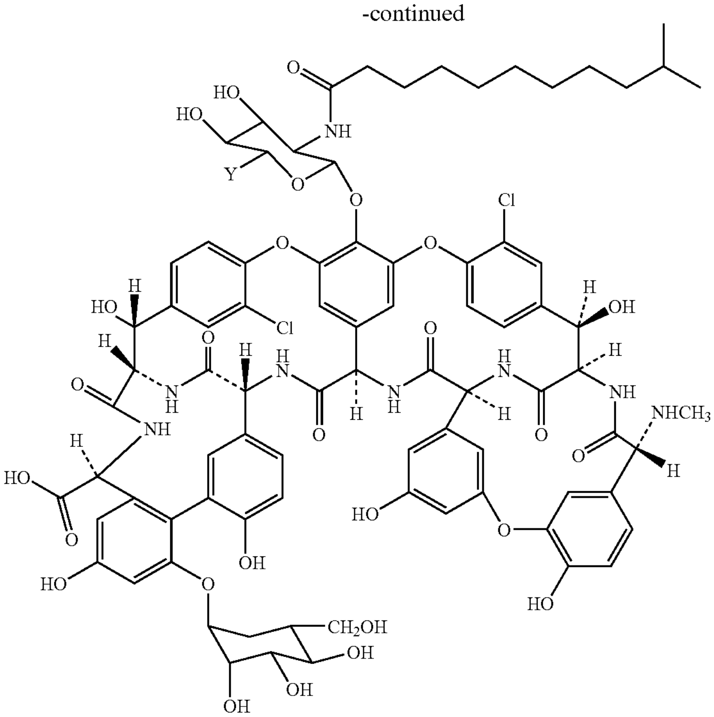

(Y = COOH, COOMe, $CH_2OH$)

by a technique selected from the group consisting of, (a) acylation of the amino substituent on the amino-substituted sugar moiety of the compound with an acyl group having the structure, $—C(=O)CR_7R_{7a}NR_8R_{8a}$, (b) conversion of the acid moiety on the macrocyclic ring of the compound with a substituted amide as defined by $R_2$, and (c) a combination of (a) and (b)

(d) a combination of (b) and acylation of the amino substituent on the amino-substituted sugar moiety of the compound with an acyl group having the structure, $—C(=O)R_6$, (e) a combination of (b) and alkylation of the amino substituent on the amino-substituted sugar moiety of the compound with an alkyl group having the structure, $CHR_5R_{5a}$, to form a compound having a formula selected from the group consisting of:

1

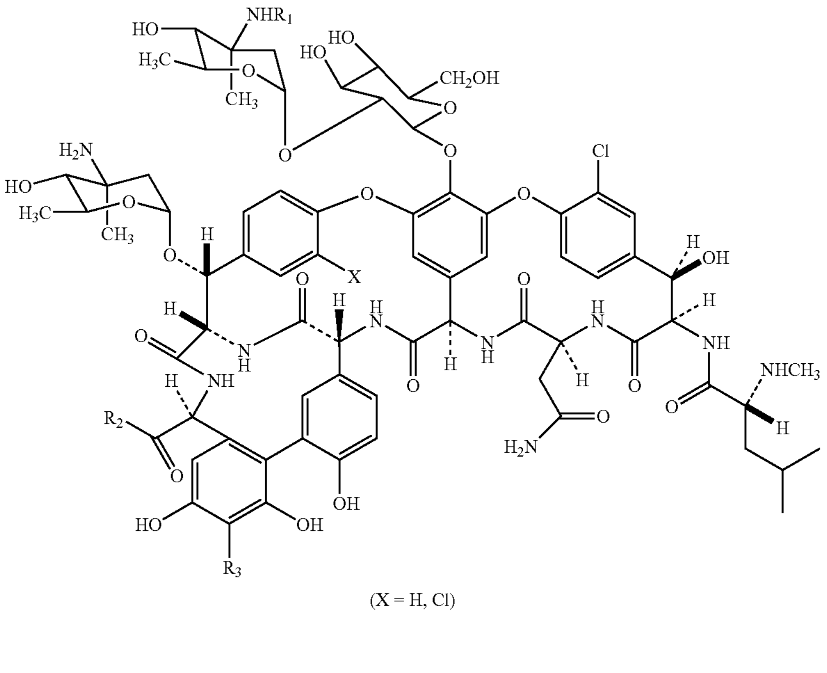

(X = H, Cl)

-continued
2
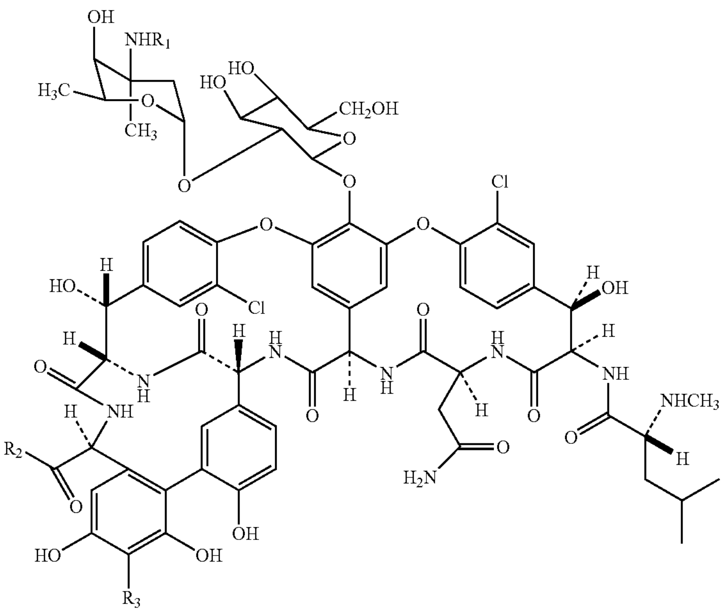
3
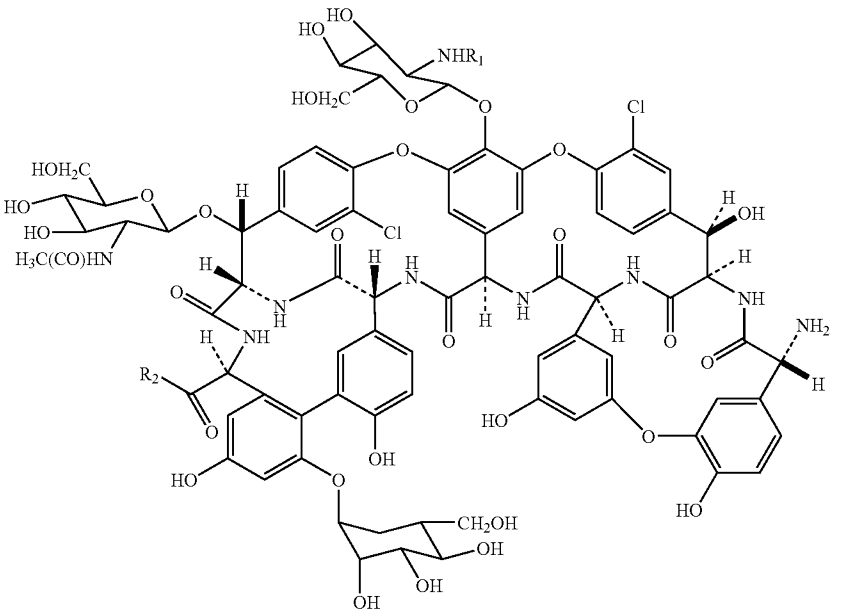

-continued
4
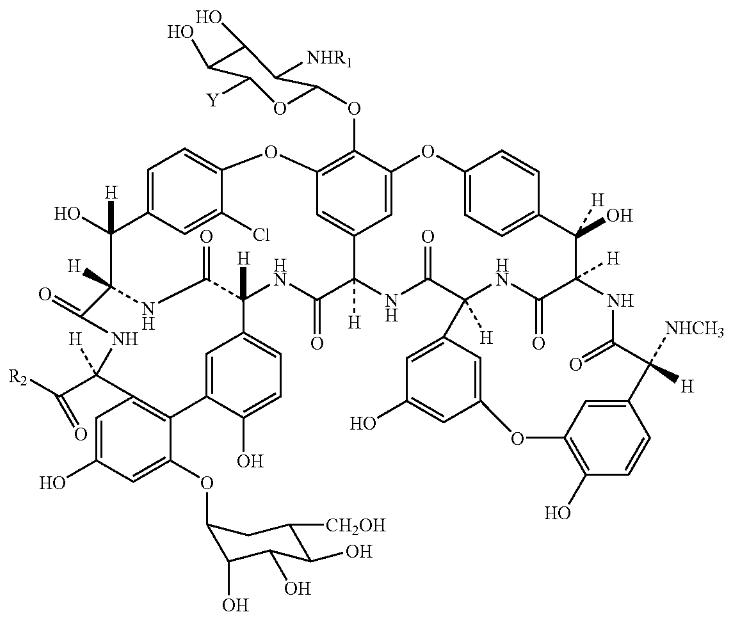
(Y = COOH, COOMe, $CH_2OH$)
1A
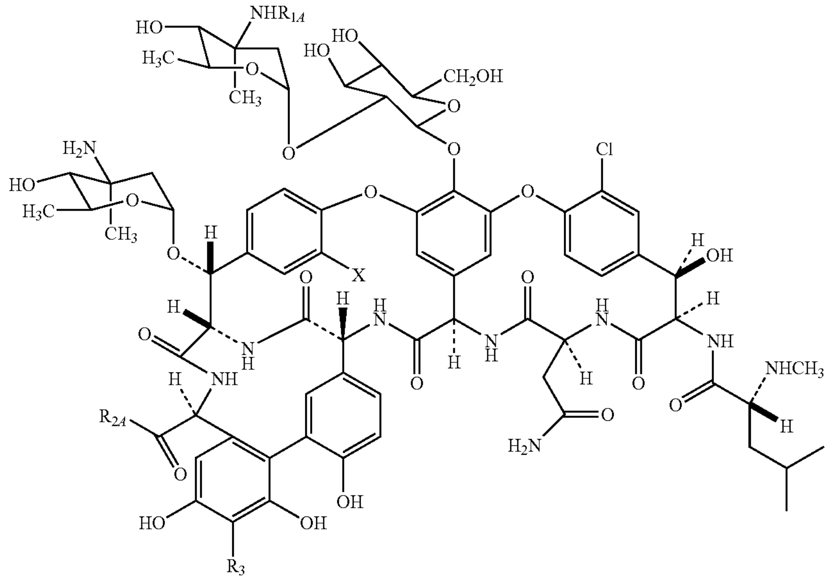
(X = H, Cl)

-continued
2A
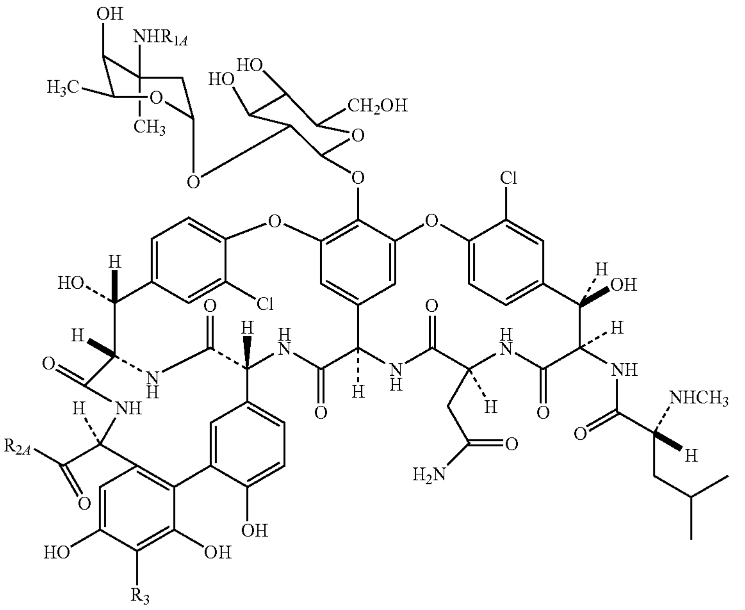
3A
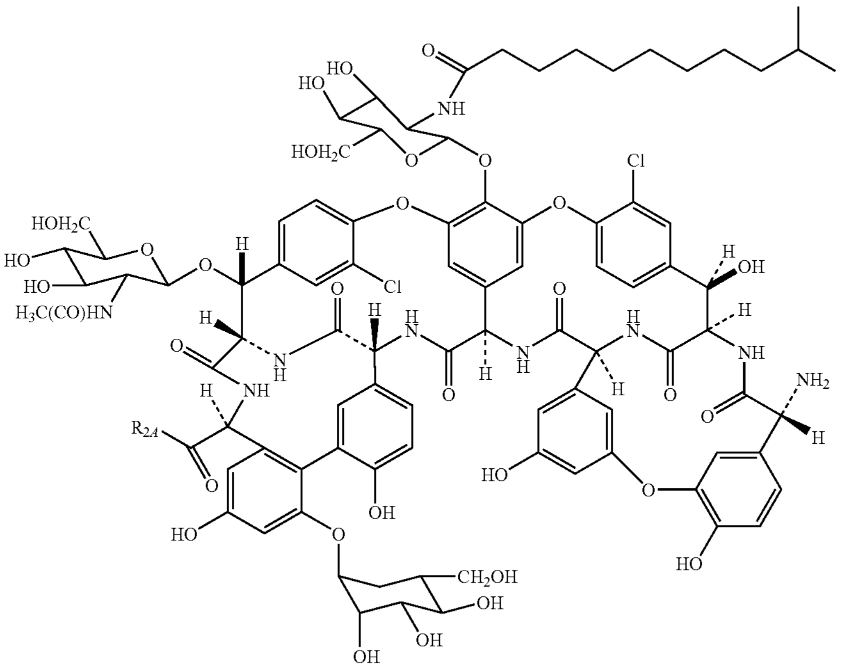

-continued

4A

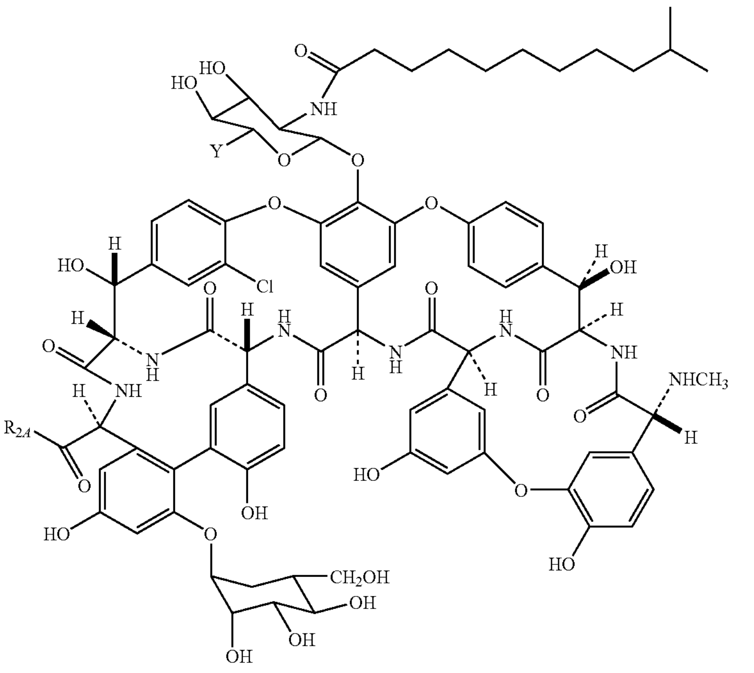

(Y = COOH, COOMe, $CH_2OH$)

wherein $R_1$, $R_{1A}$, $R_2$, $R_{2A}$, $R_3$, $R_5$, $R_{5a}$, $R_6$, $R_7$, $R_{7a}$, $R_8$, and $R_{8a}$ are as defined herein.

Synthesis of compounds may also involve the use of protecting or blocking groups in order to maximize yields, minimize unwanted side products, or improve the ease purification. Specific examples of syntheses for compounds in accordance with the present invention are provided in the Examples, below.

Pharmaceutical Compositions

Pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray, or a liquid aerosol or dry powder formulation for inhalation.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form may be accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations may also be prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions of the invention may also be formulated for delivery as a liquid aerosol or inhalable dry powder. Liquid aerosol formulations may be nebulized predominantly into particle sizes that can be delivered to the terminal and respiratory bronchioles where bacteria reside in patients with bronchial infections, such as chronic bronchitis and pneumonia. Pathogenic bacteria are commonly present throughout airways down to bronchi, bronchioli and lung parenchema, particularly in terminal and respiratory bronchioles. During exacerbation of infection, bacteria can also be present in alveoli. Liquid aerosol and inhalable dry powder formulations are preferably delivered throughout the endobronchial tree to the terminal bronchioles and eventually to the parenchymal tissue.

Aerosolized formulations of the invention may be delivered using an aerosol forming device, such as a jet, vibrating porous plate or ultrasonic nebulizer, preferably selected to allow the formation of a aerosol particles having with a mass medium average diameter predominantly between 1 to 5 μ. Further, the formulation preferably has balanced osmolarity ionic strength and chloride concentration, and the smallest aerosolizable volume able to deliver effective dose of the compounds of the invention to the site of the infection. Additionally, the aerosolized formulation preferably does not impair negatively the functionality of the airways and does not cause undesirable side effects.

Aerosolization devices suitable for administration of aerosol formulations of the invention include, for example, jet, vibrating porous plate, ultrasonic nebulizers and energized dry powder inhalers, that are able to nebulize the formulation of the invention into aerosol particle size predominantly in the size range from 1-5 μ. Predominantly in this application means that at least 70% but preferably more than 90% of all generated aerosol particles are within 1-5 μ range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AeroNeb™ and AeroDose™ vibrating porous plate nebulizers (AeroGen, Inc., Sunnyvale, Calif.), Sidestream® nebulizers (Medic-Aid Ltd., West Sussex, England), Pari LC® and Pari LC Star® jet nebulizers (Pari Respiratory Equipment, Inc., Richmond, Va.), and Aerosonic™ (DeVilbiss Medizinische Produkte (Deutschland) GmbH, Heiden, Germany) and UltraAire® (Omron Healthcare, Inc., Vernon Hills, Ill.) ultrasonic nebulizers.

Compounds of the invention may also be formulated for use as topical powders and sprays that can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 2000 mg of the compound(s) of this invention per day in single or multiple doses.

EXAMPLES

The following examples provide details concerning the synthesis, properties and activities and applications of semi-synthetic glycopeptides in accordance with the present invention. It should be understood the following is representative only, and that the invention is not limited by the detail set forth in these examples.

Example 1

Synthesis of N'-Alkylaminoacylated Eremomycin and Vancomycin Derivatives

N'-Alkylaminoacylated eremomycin or vancomycin derivatives were prepared by the treatment of unprotected eremomycin or vancomycin with $RCH_2N(Fmoc)CH_2COOSu$ (where R=p-BuPh, p-ClPhPh, p-BuOPh and p-octylOPh) followed by deprotection with 10% diethylamine in DMSO. Eremomycin derivatives were obtained in 30-50% summary yields. Vancomycin derivatives were obtained in 30-60% summary yields. The starting glycine derivatives were synthesized as shown and described below in Scheme 1 and the associated description of steps I, II and III.

Scheme 1.
Synthesis of the starting reagents for
N'-(p-OctylOPh$CH_2NHCH_2CO$)vancomycin $H_2NCH_2COOH$
RCHO, 0.5 eq
$NaCNBH_3$, 1.5 eq
$RCH_2HNCH_2COOH$ + $(RCH_2)_2NCH_2COOH$
FmocOSu, 1.5 eq.
$Et_3N$, 3 eq
$RCH_2NFmocCH_2COOH$
HOSu, 1.4 eq.
DCC, 1.2 eq
$RCH_2NFmocCH_2COOSu$ I. Reductive Alkylation of Glycine (Synthesis of $RCH_2NHCH_2COOH$).

To a stirred solution of glycine (2 mmol) in $THF:H_2O$ mixture (1:1) at room temperature a solution of 1 mmol of an appropriate aldehyde in THF and 1.5 mmol of $NaCNBH_3$ were added portion-wise. The reaction mixture was stirred for 4 h, then water was added. The resulting mixture was evaporated under vacuum to remove THF and was extracted with petroleum ether three times. Then the aqueous fraction was evaporated under vacuum with silicagel to dryness and applied to a chromatographic column with silicagel preequilibrated with $CHCl_3$. The column was eluted with a $CHCl_3$:MeOH:25% $NH_4OH$ (3:1:0.05) system at a rate 10 mL/h, while collecting 5 mL fractions. The suitable fractions were combined and evaporated under vacuum to dryness. The yields were 30-50%.

II. Synthesis of $RCH_2N(Fmoc)CH_2COOH$

To a stirred solution of $RCH_2NHCH_2COOH$ (1 mmol) in $THF:H_2O$ mixture (1:1) at room temperature 3 mmol of triethylamine and a solution of 1.5 mmol of FmocOSu in THF were added portion-wise. The reaction mixture was stirred for 4 h, then water was added. The resulting mixture was evaporated under vacuum to remove THF and was extracted with petroleum ether three times. Then the aqueous fraction was evaporated under vacuum with silicagel to dryness and applied to a chromatographic column with silicagel preequilibrated with $CHCl_3$. The column was eluted with a $CHCl_3$:MeOH:25% $NH_4OH$ (5:1:0.05) system at a rate 10 mL/h, while collecting 5 mL fractions. The suitable fractions were combined and evaporated under vacuum to dryness. The yields were 50-80%.

III. Synthesis of $RCH_2N(Fmoc)CH_2COOSu$

To a stirred solution of $RCH_2N(Fmoc)CH_2COOH$ (1 mmol) in $CH_2Cl_2$ at 0-5° C. 1.3 mmol of HOSu were added and a solution of 1.2 mmol of DCC in THF was added dropwise. The reaction mixture was stirred for 4 hours, then a precipitate of dicyclohexylurea was filtered off. The organic layer was concentrated under vacuum to a small volume and a precipitated solid of dicyclohexylurea was filtered off again. The organic layer was evaporated under vacuum to dryness.

Preparation of N'-(p-OctylOPh$CH_2NHCH_2$CO)vancomycin

P-OctylOPh$CH_2N(Fmoc)CH_2$COOSu was prepared as shown at the Scheme 1 in 20% summary yield starting from glycine.

Then, to a stirred solution of 1800 mg (1.25 mmol) of vancomycin (base) in a 30 mL $DMSO:H_2O$ (4:1) mixture, 0.16 mL (1.25 mmol) of $Et_3N$ and 1165 mg (1.9 mmol) of p-octylOPh$CH_2N(Fmoc)CH_2$COOSu were added. The reaction mixture was stirred at room temperature for 5 h, then 3 mL of $Et_2NH$ were added. The reaction mixture was stirred at room temperature for 1 h, then it was added to 200 mL of acetone. A solid precipitate was filtered off, washed with acetone and dried under vacuum. The resulting dry precipitate was then dissolved in a $H_2O$:THF (1:1) mixture and evaporated with a small amount of silanized silicagel under vacuum. This solution was applied to a chromatographic column with silanized silicagel (3×120 cm) preequilibrated with $H_2O$. The column was eluted firstly with $H_2O$ (1000 mL) at a rate 10 mL/h, while collecting 5 mL fractions. The fractions containing vancomycin were collected. The column was then eluted with 0.02 M CH3COOH (1000 mL) at a rate 10 mL/h, while collecting 5 mL fractions. Then the column was eluted with 15% MeOH in 0.02 M CH3COOH (500 mL) at the same rate, and the fractions containing the product of the reaction were collected. Then the column was eluted with 30% MeOH in 0.02 M CH3COOH (1000 mL) at the same rate, and the suitable fractions containing the product of the reaction were collected. All the suitable fractions of N'-{p-octylOPh$CH_2NHCH_2$CO)vancomycin were combined and concentrated under vacuum to a small volume (~10 mL). Then 30 mL of acetone were added and this mixture was added to 250 mL of $Et_2O$ to precipitate the product. A solid precipitate was filtered off, washed with $Et_2O$, and dried under vacuum to give 904 mg (42%) of N'-{p-octylOPh$CH_2NHCH_2$CO)vancomycin.

The purification of the eremomycin and vancomycin derivatives synthesized in this manner was performed using column chromatography on silanized silica gel. The progress of the reactions, the components of the column eluates and the purity of the final compounds were checked by TLC in the systems: EtOAc-n-PrOH-25% $NH_4OH$ 1:1:1 or 3:2:2 and n-BuOH—AcOH—$H_2O$ 5:1:1. Additionally, the purity of the derivatives for in vivo study was controlled by HPLC.

Example 2

Preparation of N'-[$C_8H_{17}OC_6H_4CH_2NHCH(CH_3)$CO] Vancomycin

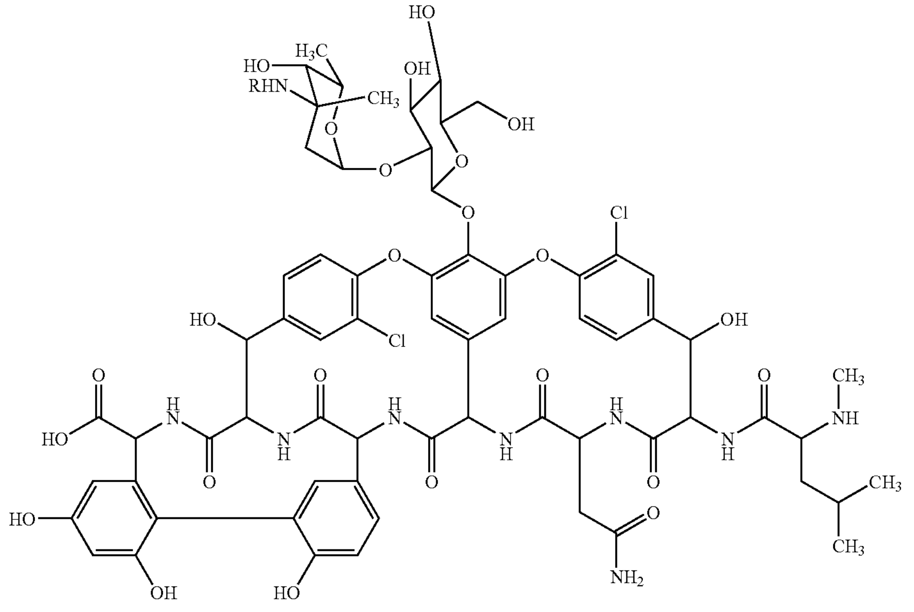

| Cmpd | R | chemical formula | MW |
|---|---|---|---|
| 301 | p-$C_8H_{17}$0BnNHCH($CH_3$)CO | $C_{84}H_{102}N_{10}O_{26}Cl_2$ | 1736.6 |

Scheme 2.
Synthesis of the starting reagents for
N'-[$C_8H_{17}OC_6H_4CH_2NHCH(CH_3)CO$]vancomycin

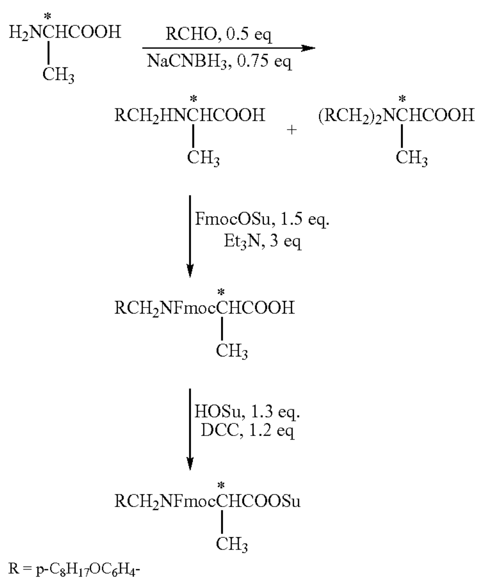

I. Reductive Alkylation of L-alanine (Synthesis of p-$C_8H_{17}OC_6H_4CH_2NHCH(CH_3)COOH$)

To a stirred solution of L-alanine (1 mmol) in THF-$H_2O$ mixture (1:1) at 26-28° C. a solution of 1 Mmol of p-$C_8H_{17}OC_6H_4CHO$ in THF and 0.75 mmol of $NaCNBH_3$ were added portion-wise. The reaction mixture was stirred at 26-28° C. for 4 h, then water was added. The resulting mixture was evaporated under vacuum to remove THF and to precipitate the product of the reaction. The precipitate was filtered off and washed with icy cold water. The solid was dissolved in THF-$H_2O$ mixture (1:1) and this mixture was kept at 5° C. for 18 h. A white solid (L-alanine) was filtered off and washed with icy cold water, the filtrate was evaporated under vacuum to remove THF and to precipitate the product of the reaction. The precipitate was washed with acetone and dried under vacuum. The yield was about 30-40%.

II. Synthesis of p-$C_8H_{17}OC_6H_4CH_2NFmocCH_2(CH_3)$ COOH

To a stirred solution of N-(p-$C_8H_{17}OC_6H_4CH_2$)-(L)-alanine (1 mmol) in THF-$H_2O$ mixture (1:1) at room temperature 3 mmol of triethylamine and a solution of 1.5 mmol of FmocOSu in THF were added portion-wise. The reaction mixture was stirred for 4 h, then water was added. The resulting mixture was evaporated under vacuum to remove THF and was extracted with petroleum ether. The organic layer was washed with water. The aqueous fractions were combined, evaporated under vacuum with silica gel to dryness and applied to a chromatographic column with silica gel pre-equilibrated with $CHCl_3$. The column was eluted with a $CHCl_3$:MeOH:25% $NH_4OH$ (5:1:0.05) system at a rate 10 mL/h, while collecting 5 mL fractions. The suitable fractions were combined and evaporated under vacuum to dryness. The yield was about 60-80%.

III. Synthesis of p-$C_8H_{17}OC_6H_4CH_2NFmocCH(CH_3)$ COOSu

To a stirred solution of p-$C_8H_{17}OC_6H_4CH_2NFmocCH$ $(CH_3)COOH$ (1 mmol) in $CH_2Cl_2$ at 0-5° C. 1.3 mmol of HOSu was added and, afterwards, a solution of 1.2 mmol of DCC in THF drop-wise. The reaction mixture was stirred for 4 h, then the precipitate of dicyclohexylurea was filtered off. The organic layer was concentrated under vacuum to a small volume and a precipitated solid of dicyclohexylurea was filtered off again. The organic layer was evaporated under vacuum to dryness. P—$C_8H_{17}OC_6H_4CH_2NFmocCH(CH_3)$ COOSu was obtained in summary yield of about 20-30% starting from L-alanine according to Scheme 2.

Synthesis of N'-[$C_8H_{17}OC_6H_4CH_2NHCH(CH_3)CO$]Vancomycin

To a stirred solution of 360 mg (0.25 mmol) of vancomycin (base) in 7.5 mL a DMSO-$H_2O$ (4:1) mixture 32 μL (0.25 mmol) of triethylamine and 627 mg (0.38 mmol) of starting amino acid derivative p-$C_8H_{17}OC_6H_4CH_2NFmocCH(CH_3)$ COOSu were added. The reaction mixture was stirred at room temperature for 5 h, then 0.75 mL of $Et_2NH$ were added. The reaction mixture was stirred at room temperature for 1 h, then it was added to 100 mL of acetone. A solid precipitate was filtered off, washed with acetone and dried under vacuum. Then it was dissolved in an $H_2O$-THF (1:1) mixture, evaporated with a small amount of silinized silica gel under vacuum and applied to a chromatographic column with silinized silica gel (2×60 cm) preequilibrated with $H_2O$. The column was eluted firstly with $H_2O$ (200 mL) at a rate 10 mL/h, while collecting 5 mL fractions. The column was eluted with 0.02 M $CH_3COOH$ (300 mL) at a rate 10 mL/h, while collecting 5 mL fractions. The fractions containing vancomycin were collected. Then the column was eluted with 10% MeOH in 0.02 M CH3COOH (250 mL) at the same rate followed with 20% MeOH in 0.02 M $CH_3COOH$ (250 mL) to elute side products. The fractions containing the desired product were collected when the column was eluted with 40% MeOH in 0.02 M $CH_3COOH$. All the suitable fractions of the product were combined and concentrated under vacuum to a small volume (~2 mL). THF (2 mL) was added then 20 mL of acetone were added to this mixture. The resulting mixture was added to 80 mL of $Et_2O$ to precipitate the reaction product. A solid precipitate was filtered off and washed with acetone, then dried in vacuum. The yield was 130 mg (30%).

Example 3

Synthesis of N'-Aminoacyl (Non-Glycyl) Derivatives of Eremomycin

N'-Acylated eremomycin derivatives substituted with amino acids or N-alkylated amino acids and a vancomycin derivative were prepared by the treatment of an antibiotic with N-hydroxysuccinimide ester of N-Fmoc-derivatives of amino acids or N-alkylated amino acids, followed by deprotection with 10% diethylamine in DMSO gave a desirable product in 10-50% summary yields. The starting derivatives of amino acids were synthesized as shown and described below with reference to Scheme 3.

Scheme 3.

Preparation of the starting amino acids derivatives for N'-aminoacyl (non-glycyl) Derivatives of Eremomycin:

a) N-hydroxysuccinimide ester of $N^{\alpha}$, $N^{\epsilon}$-di-Fmoc-L-Lys

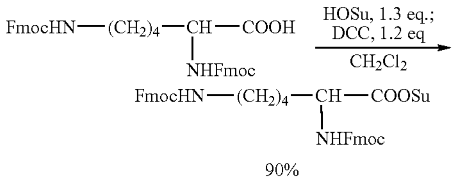

b) N-hydroxysuccinimide ester of N-Fmoc-L-Phe, N-Fmoc-D-Phe and N-Fmoc-(Bn-O-L-Tyr):

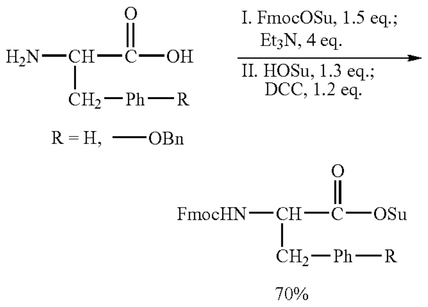

c) N-hydroxysuccinimide ester of $N^{\alpha}$-R-$N^{\alpha}$, $N^{\delta}$-di-Fmoc-L-Orn:

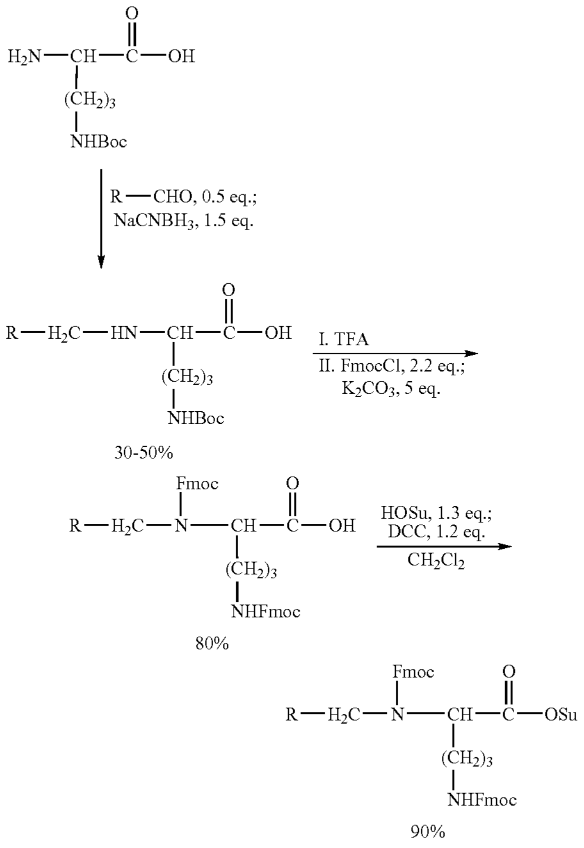

where R = p-(Bu-Ph)-, p-($C_8H_{17}$-O-Ph)-

Preparation of N-Hydroxysuccinimide Ester of $N^{\alpha}$,$N^{\epsilon}$-di-Fmoc-L-Lys (Scheme 3a)

N-Hydroxysuccinimide ester of $N^{\alpha}$,$N^{\epsilon}$-di-Fmoc-L-Lys was obtained from $N^{\alpha}$,$N^{\epsilon}$-di-Fmoc-L-Lys by the method C (see below).

Preparation of N-hydroxysuccinimide Ester of N-Fmoc-L-Phe and N-Fmoc-D-Phe (scheme 3b).

N-Hydroxysuccinimide ester of N-Fmoc-L-Phe was obtained by the method C from N-Fmoc-L-Phe, prepared from L-Phe by the method B.

Preparation of N-Hydroxysuccinimide Ester of N-Fmoc-(Bn-O-L-Tyr) (Scheme 3b).

N-Fmoc-(Bn-O-L-Tyr) was obtained starting from Bn-O-L-Tyr by the method B. N-hydroxysuccinimide ester of N-Fmoc-(Bn-O-L-Tyr) was prepared by the method C.

Preparation of N-Hydroxysuccinimide Ester of $N^{\alpha}$—R—$N^{\alpha}$, $N^{\delta}$-di-Fmoc-L-Orn (Scheme 3c).

$N^{\alpha}$—R—$N^{\delta}$-Boc-L-Om [R=p-($C_8H_{17}$—O-Ph)—$CH_2$— or p-(BuPh)—$CH_2$—] was obtained from $N^{\delta}$-Boc-L-Om and R—CHO by the method A. Then $N^{\alpha}$—R—$N^{\delta}$-Boc-L-Om was treated by TFA at room temperature for 30 min to give $N^{\alpha}$—R-L-Orn. MeOH was added and the solution was evaporated under vacuum to dryness. This operation was repeated for 3 times. $N^{\alpha}$—R—$N^{\alpha}$,$N^{\delta}$-di-Fmoc-L-Om was obtained starting from $N^{\alpha}$—R-L-Orn as described in method B, but a solution of 2.2 eq. of FmocCl in THF was added dropwise to a cooled (0-5° C.) solution of 1 eq. of $N^{\alpha}$—R-L-Om and 5 eq. of $K_2CO_3$ in a THF-$H_2O$ (1:1) mixture. N-hydroxysuccinimide ester of $N^{\alpha}$—R—$N^{\alpha}$,$N^{\delta}$-di-Fmoc-L-Orn was prepared by the method C.

Method A. Reductive Alkylation

To a stirred solution of an $N^{\delta}$-Boc-L-Orn (2 mmol) in THF:$H_2O$ mixture (1:1) at room temperature a solution of 1 mmol of an appropriate aldehyde in THF and 1.5 mmol of $NaCNBH_3$ were added portion-wise. The reaction mixture was stirred for 4 h, then water was added. The resulting mixture was evaporated under vacuum to remove THF and was extracted with petroleum ether. The aqueous fraction was evaporated under vacuum with silica gel to dryness and applied to a chromatographic column with silica gel pre-equilibrated with $CHCl_3$. The column was eluted with a $CHCl_3$:MeOH:25% $NH_4OH$ (5:1:0.05) system at a rate 10 mL/h, while collecting 5 mL fractions. The suitable fractions were combined and evaporated under vacuum to dryness. The yields were 30-50%.

Method B. Preparation of N-Fmoc Derivatives

To a stirred solution of amino acid (1 mmol) in THF:$H_2O$ mixture (1:1) at room temperature 4 mmol of triethylamine and a solution of 1.5 mmol of FmocOSu in THF were added portion-wise. The reaction mixture was stirred for 4 h, then water was added. The resulting mixture was evaporated under vacuum to remove THF and was extracted with petroleum ether. The aqueous fraction was evaporated under vacuum with silica gel to dryness and applied to a chromatographic column with silica gel preequilibrated with $CHCl_3$. The column was eluted with a $CHCl_3$:MeOH:25% $NH_4OH$ (5:1:0.05), according to Scheme 2b, or a (7:1:0.05), according to Scheme 2c, system at a rate 10 mL/h, while collecting 5 mL fractions. The suitable fractions were combined and evaporated under vacuum to dryness. The yields were 50-80%.

Method C. Preparation of N-Hydroxysuccinimide Ester

To a stirred solution of starting N-Fmoc derivative (1 mmol) in $CH_2Cl_2$ at 0-5° C. 1.3 mmol of HOSu were added and a solution of 1.2 mmol of DCC in THF was added dropwise. The reaction mixture was stirred for 4 h, then the precipitate of dicyclohexylurea was filtered off. The organic layer was concentrated under vacuum to a small volume and a precipitated solid of dicyclohexylurea was filtered off again. The organic layer was evaporated under vacuum to dryness.

Preparation of N'-Substituted Glycipeptide Derivatives

To a stirred solution of 0.5 mmol of an antibiotic (base) in 15 mL DMSO:$H_2O$ (4:1) mixture 0.5 mmol of triethylamine and 0.75 mmol of starting amino acid derivative, prepared according to scheme 2, were added. The reaction mixture was stirred at room temperature for 5 h, then 1.5 mL of $Et_2NH$ weas added. The reaction mixture was stirred at room temperature for 1 h, then it was added to 100 mL of acetone. A solid precipitated was filtered off, washed with acetone and dried under vacuum. Then it was dissolved in a $H_2O$:THF (1:1) mixture, evaporated with a small amount of silanized silica gel under vacuum and applied to a chromatographic column with silanized silica gel (3×120 cm) preequilibrated with $H_2O$. The column was eluted firstly with $H_2O$ (400 mL) at a rate 10 mL/h, while collecting 5 mL fractions. The column was then eluted with 0.02 M $CH_3COOH$ (500 mL) at a rate 10 mL/h, while collecting 5 mL fractions. The fractions containing an antibiotic were collected. Then the column was eluted with 10% MeOH in 0.02 M CH3COOH (500 mL) at the same rate, and the fractions containing the product of the reaction were collected. Then the column was eluted with 20% MeOH in 0.02 M $CH_3COOH$ (500 mL), then 30% MeOH in 0.02 M $CH_3COOH$ at the same rate, and the suitable fractions containing the product of the reaction were collected. All the suitable fractions of desirable product were combined and concentrated under vacuum to a small volume (~3 mL). Then 50 mL of acetone were added to precipitate the products N-hydroxysuccinimide ester of $N^{\alpha}$,$N^{\epsilon}$-di-Fmoc-L-Lys and N-hydroxysuccinimide ester of N-Fmoc-L-Phe, N-Fmoc-D-Phe and N-Fmoc-(Bn-O-L-Tyr). For N-hydroxysuccinimide ester of $N^{\alpha}$—R—$N^{\alpha}$,$N^{\delta}$-di-Fmoc-L-Om, 8 mL of acetone were added and this mixture was added to 100 mL of $Et_2O$ to precipitate the product. A solid precipitated was filterred off and washed with acetone or $Et_2O$, then dried under vacuum. The yields were 30-50% for N-hydroxysuccinimide ester of $N^{\alpha}$,$N^{\epsilon}$-di-Fmoc-L-Lys and N-hydroxysuccinimide ester of N-Fmoc-L-Phe, N-Fmoc-D-Phe and N-Fmoc-(Bn-O-L-Tyr) and about 10% for N-hydroxysuccinimide ester of $N^{\alpha}$—R—$N^{\alpha}$,$N^{\delta}$-di-Fmoc-L-Om.

Example 4

Preparation of (Adamantylamino)Amides of Glycopeptide Antibiotics or their Derivatives To a stirred solution of an antibiotic or its derivative (e.g., prepared as described in Example 3) (0.1 mmol) in DMSO (4 mL) 2-amino-adamantan or 1-amino-adamantane (0.5 mmol), $Et_3N$ (1 mmol) and HBPyU [O-benzotriazol-1-yl-N,N,N',N'-bis(tetramethylene)uronium hexafluorophosphate] or PyBOP [benzotriazol-1-yloxy)-tris-(pyrrolidino) phosphonium-hexafluorophosphate] (0.2 mmol) were added at room temperature in three portions with stirring over 1 h. After 4 h acetone (100 mL) was added to give a solid, which was washed with acetone and dried under vacuum to give the corresponding amide in about 90% yield.

Example 5

Additional Amide Derivatization and Evaluation

The synthesis of amides of eremomycin was performed by the condensation of unprotected eremomycin with an appropriate amine in the presence of PyBOP as a condensing agent, according to procedures described in Miroshnikova O. V., Printsevskaya S. S., Olsufyeva E. N., Pavlov A. Y., Nilius A., Hensey-Rudloff D., Preobrazhenskaya M. N. J. Antibiot., 2000. V.53. P. 286-293, incorporated herein by reference for all purposes. The yields of the amides depend on the nature of the amines and were 40-80% (e.g., the yield of Compound 79 was 40%, while Compound 90 was obtained in 80% yield). Most of the starting amines were not available commercially and were prepared as shown in Scheme 4.

The aminomethylated derivatives of eremomycin were obtained by the interaction of eremomycin with an amine and 37% aqueous formaldehyde at pH 9-9.5 according to procedures described in Pavlov A. Y., Lazhko E. I., Preobrazhenskaya M. N. J. Antibiot. 1996, V. 50, P. 509-513, incorporated herein by reference for all purposes. In contrast to eremomycin amides, the synthesis of the aminomethylated derivatives gave better yields for secondary amines than for primary amines (e.g., Compound 72-40% and Compound 73-60%).

The amides of the aminomethylated derivatives were prepared by the amidation of the aminomethylated derivatives. The best results were obtained by the amidation with the usage of an amine excess (~5 times). The summary yields of the amides of the aminomethylated derivatives (starting from eremomycin) were 20-50%.

The amides of N-allyl-eremomycin and quaternary salt of N,N-dimethyl-eremomycin were obtained by the reaction of the appropriate amide with allyl bromide or methyl iodide in DMSO in the presence of $NaHCO_3$. In the case of allyl bromide the yield of the product was about 60%, while methyl iodide gave 90% yield of the target amide of N,N-dimethyl-eremomycin. Thus the summary yield of these derivatives was 45-70%. The decyldimethylaminopropylamide of N,N-dimethyl-eremomycin (Compound 70 was prepared with 65% yield.

The purification of the derivatives of eremomycin was performed using column chromatography on CM-32-cellulose or silanized silica gel as described in Pavlov A. Y., Berdnikova T. F., Olsufyeva E. N., Miroshnikova O. V., Fillipposianz S. T., Preobrazhenskaya M. N., Sottani C., Colombo L., Goldstein B. P. J. Antibiot., 1996, V. 49, P. 194-198; and Miroshnikova O. V., Printsevskaya S. S., Olsufyeva E. N., Pavlov A. Y., Nilius A., Hensey-Rudloff D., Preobrazhenskaya M. N. J. Antibiot., 2000. V.53. P. 286-293, incorporated herein by reference for all purposes. The progress of the reactions, the components of the column eluates and the purity of the final compounds were checked by TLC in the systems: EtOAc-n-PrOH-25% $NH_4OH$ 1:1:1 or 3:2:2 and n-BuOH—AcOH—$H_2O$ 5:1:1. Additionally, the purity of the most active derivatives was controlled by HPLC. The structures of the eremomycin derivatives were confirmed by $^1H$ NMR and by the methods of chemical degradation (acid hydrolysis yielding unmodified eremosamine and altered aglycon and also Edman's degradation that shows the presence of the unsubstituted N-terminal amino acid), according to procedures described in the references noted above.

Scheme 4.
Synthesis of the starting amines a) The amine for Compounds 46 and 72 was obtained as follows:

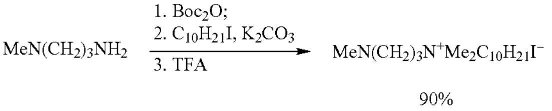

The amine for Compounds 74 and 79 was obtained from N-methylpiperazine by the similar procedure in 90% yield.

b) Amines for Compounds 89, 90, 95 and 96 were obtained as follows:

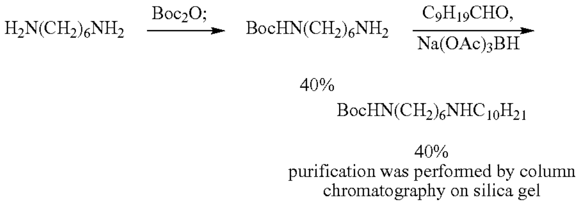

The amine for Componds 84 and 87 was prepared from piperazine by the similar method in 30% summary yield.

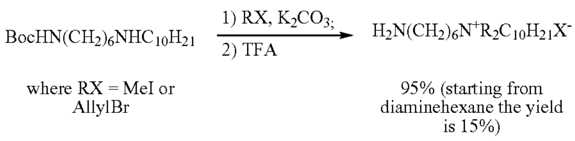

The amine for Compound 96 was obtained from diaminohexane in 10% overall yield.

-continued c) Amines for Compounds 88 and 91 were prepared as follows:

Boc-Lys(Boc)OSu → 1. $H_2N(CH_2)_3N^+Me_2C_{10}H_{21}I^-$; 2. TFA → $LysHN(CH_2)_3N^+Me_2C_{10}H_{21}I^-$ 90%

$BocHN(CH_2)_5COOH$ → 1. DCC, HOSu, $H_2N(CH_2)_3N^+Me_2C_{10}H_{21}$; 2. TFA → $H_2N(CH_2)_5CONH(CH_2)_3N^+Me_2C_{10}H_{21}I^-$ 85%

Example 6

Antibacterial Evaluation

Antibacterial activity in vitro was investigated by broth microdilution method in Meuller-Hinton broth as recommended by NCCLS. All strains tested were clinical isolates either sensitive or resistant to natural glycopeptides. Results are reported in the tables as MIC (minimal inhibitory concentration) in μg/ml. Most of the compounds synthesized have activity comparable with vancomycin against sensitive bacteria, Compound 70 being an exception. It is the most active derivative of eremomycin among all the compounds investigated against clinical isolates of vancomycin sensitive gram-positive bacteria. All derivatives of eremomycin are more active than natural glycopeptides (Ere, Vanco, Teico) against GISA and GRE. Compounds 72, 87, 90 and 95 are the most active against GISA. Compounds 70, 72, 75, 76, 90 and 95 demonstrate also rather good activity against GRE strains (between 4-16 mcg/ml), however some lower than LY 333328.

Analysis of the MIC values obtained shows that the introduction of a moiety containing the quaternary fragment —$N^+R_1R_2C_{10}H_{21}$ presents a productive approach to the synthesis of derivatives with high activity against GISA and GRE. The positive influence of quartenization on antibacterial activity is clearly seen after comparison of MIC values for Compound 89 with that for Compounds 90 or 95. The transformation of the group —$NHC_{10}H_{21}$ (89) into —$N^+Me_2C_{10}H_{21}$ (90) or —$N^+Allyl_2C_{10}H_{21}$ (95) leads to the increase of the activity up to 2-8 times against sensitive and resistant bacteria. It is interesting also to note that Compounds 92 and 96 containing two $C_{10}H_{21}$ moieties retain good activity against both resistant and sensitive bacteria, while earlier it was concluded that the introduction of two hydrophobic non-quartenized substituents leads to the significant decrease of antibacterial activity (more than by one order). The investigation of SAR for compounds containing the quaternary fragment —$N^+R_1R_2C_{10}H_{21}$ shows that the length of the spacer between this moiety and the framework of eremomycin (Compounds 46 and 90) has no significant influence on the antibacterial activity. The nature (hydrophobicity) of the spacer (Compounds 88, 90 and 91) seems to be more important.

Tables

The following tables identify specific species of compounds according to the present invention and information concerning their associated antibacterial activity. The glycopeptides were tested against a variety of strains, indicated below, including *Staphylococus epidermidis, Staphylococus haemolyticus*, glycopeptides-intermediate *Staphylococus aureus* (GISA), glocopeptide-sensitive *Enterococcus faecalis* (GSE), and glocopeptide-resistant *Enterococcus faecalis* (GRE). Results are shown in the table as minimum inhibitory concentration (MIC) in units of μg/ml:

TABLE 1

N'-alkylglucyl- and N'-acylglycylsubstituted eremomycin derivatives of the formula:

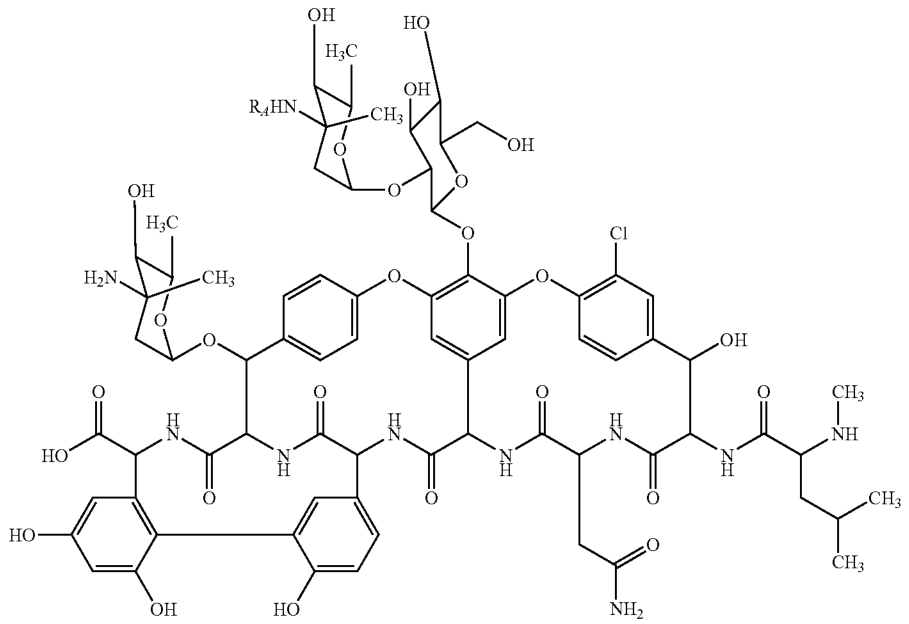

wherein $R_A$ is as indicated for each compound:

| Compound # | $R_A$ |
|---|---|
| 44 | p-Cl-PhBn $HNCH_2CO$ |
| 194 | $(C_{10}H_{21})_2HNCH_2CO$ |
| 57 | p-BuBn$HNCH_2CO$ |
| 187 | $Bu_2NBnHNCH_2CO$ |
| 293 | p-F-Bn$HNCH_2CO$ |
| 294 | p-$CF_3$-Bn$HNCH_2CO$ |
| 192 | stilbenyl$HNCH_2CO$ |
| 287 | (phenanthren-9-yl)$CH_2HNCH_2CO$ |
| 292 | (fluoren-2-yl)$CH_2HNCH_2CO$ |

-continued

| Compound # | $R_A$ |
|---|---|
| 296 | (quinolin-2-yl)$HNCH_2CO$ |
| 193 | p-BuOBn$HNCH_2CO$ |
| 214 | p-$C_8H_{17}$OBn$HNCH_2CO$ |
| 223 | p-BnOBn$HNCH_2CO$ |
| 224 | 5-BnO-(indol-3-yl)$CH_2HNCH_2CO$ |
| 225 | 1-Bn(indol-3-yl)$CH_2HNCH_2CO$ |
| 186 | $C_9H_{19}COHNCH_2CO$ |
| 221 | Fmoc$HNCH_2CO$ |
| 222 | Adoc$HNCH_2CO$ |

TABLE 1a

Antibacterial activity of N'-alkylglucyl- and N'-acylglycylsubstituted eremomycin derivatives

| Cmpd/ Strain | 533 *S. epidermidis* | 602 *S. haemolyticus* | 3797 *S. aureus* (GISA) | 3798 *S. aureus* (GISA) | 568 *E. faecium* (GSE) | 559 *E. faecalis* (GSE) | 569 *E. faecium* (GRE) | 560 *E. faecalis* (GRE) |
|---|---|---|---|---|---|---|---|---|
| 44 | 0.5 | 2 | 4 | 4 | 1 | 1 | 8 | 8 |
| 194 | 2 | 2 | 8 | 8 | 2 | 4 | 8 | 16 |
| 57 | 0.5 | 2 | 4 | 4 | 0.5 | 0.5 | 4 | 4 |
| 187 | 1 | 1 | 8 | 8 | 1 | 2 | 32 | 32 |
| 293 | 4 | 4 | 8 | 8 | 4 | 4 | 16 | 16 |
| 294 | 1 | 1 | 4 | 4 | 0.5 | 0.5 | >64 | >64 |
| 192 | 0.5 | 0.5 | 8 | 8 | 0.5 | 1 | 4 | 8 |
| 287 | 2 | 2 | 16 | 16 | 2 | 2 | >64 | >64 |
| 292 | 4 | 4 | 8 | 8 | 2 | 2 | 32 | 32 |
| 296 | 4 | 4 | >32 | >32 | 2 | 2 | >64 | >64 |
| 193 | 0.5 | 1 | 4 | 4 | 1 | 2 | 64 | 64 |
| 214 | 1 | 1 | 4 | 4 | 0.5 | 1 | 8 | 8 |
| 223 | 2 | 4 | 8 | 8 | 2 | 2 | 16 | 64 |
| 224 | 2 | 2 | 8 | 8 | 1 | 2 | 16 | >64 |
| 225 | 1 | 2 | 4 | 4 | 4 | 2 | 16 | 64 |
| 186 | 2 | 2 | 16 | 16 | 1 | 2 | >64 | >64 |
| 221 | n.t | n.t | n.t | n.t | 0.5 | 0.5 | 64 | >64 |
| 222 | n.t | n.t | n.t | n.t | 1 | 2 | >64 | >64 |

TABLE 2

N'-alkylglycylsubstituted vancomycin derivatives of the formula:

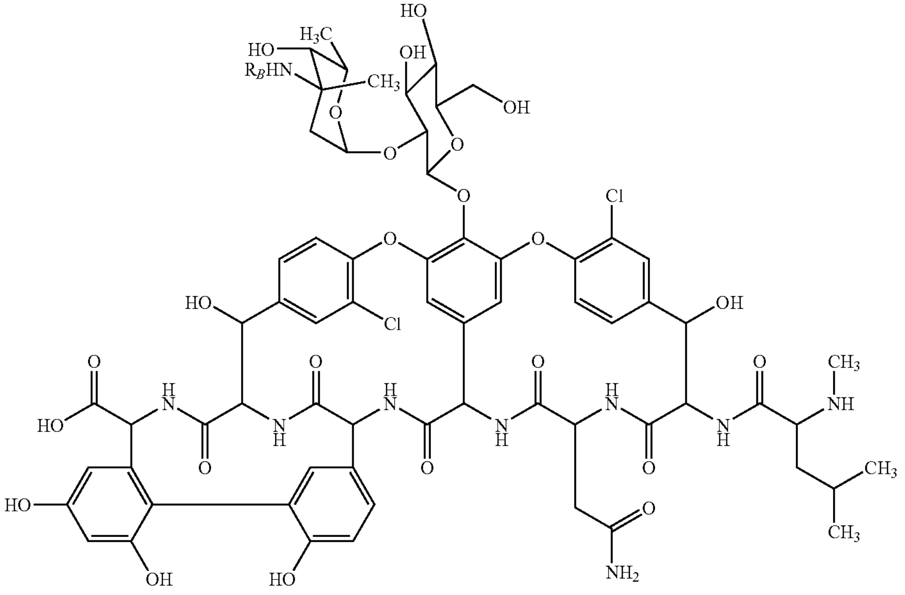

wherein $R_B$ is as indicated for each compound:

| Compound # | $R_B$ |
|---|---|
| 210 | p-Cl-PhBnHNCH$_2$CO |
| 291 | p-F-BnHNCH$_2$CO |
| 290 | p-CF$_3$-BnHNCH$_2$CO |
| 182 | p-BuBnHNCH$_2$CO |

-continued

| Compound # | $R_B$ |
|---|---|
| 218 | p-BuOBnHNCH$_2$CO |
| 220 | p-C$_8$H$_{17}$OBnHNCH$_2$CO |
| 298 | (quinolin-2-yl)HNCH$_2$CO |

TABLE 2a

Antibacterial activity of N'-alkylglycylsubstituted vancomycin derivatives

| Cmpd/ Strain | 533 *S. epidermidis* | 602 *S. haemolyticus* | 3797 *S. aureus* (GISA) | 3798 *S. aureus* (GISA) | 568 *E. faecium* (GSE) | 559 *E. faecalis* (GSE) | 569 *E. faecium* (GRE) | 560 *E. faecalis* (GRE) |
|---|---|---|---|---|---|---|---|---|
| 210 | 0.13 | 0.25 | 1 | 1 | 0.25 | 0.5 | 16 | 16 |
| 291 | 4 | 4 | 4 | 4 | 1 | 1 | 8 | 8 |
| 290 | 4 | 4 | 4 | 4 | 4 | 2 | >64 | >64 |
| 182 | 0.25 | 0.5 | 2 | 2 | 0.5 | 1 | 32 | 32 |
| 218 | 0.13 | 0.13 | 0.5 | 1 | 0.5 | 1 | >64 | >64 |
| 220 | 0.5 | 1 | 2 | 2 | 0.25 | 0.25 | 2 | 4 |
| 298 | 8 | 8 | 8 | 8 | 4 | 2 | >64 | 64 |

TABLE 3

Eremomycin derivatives N'-substituted by non-glycine amino acids having the formula:

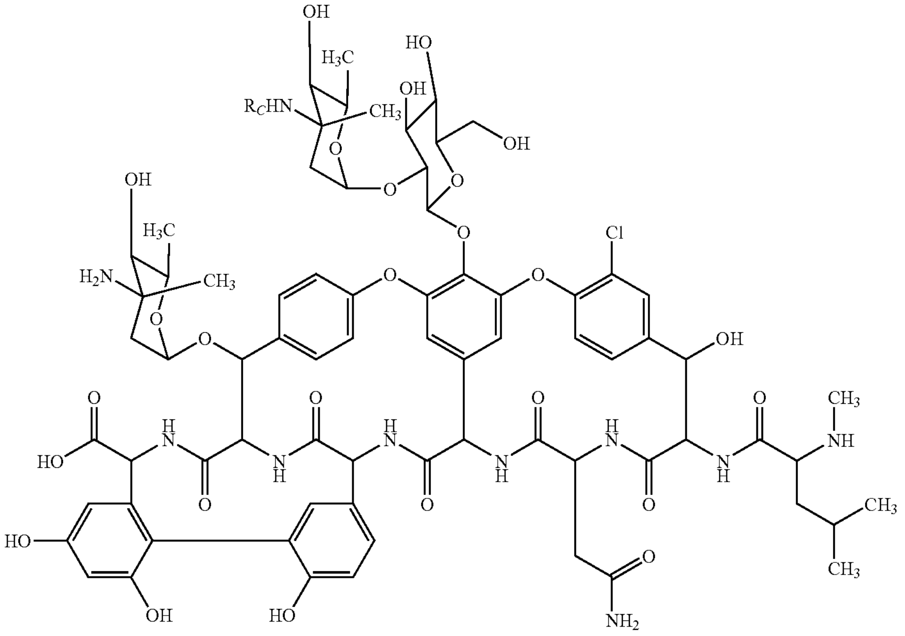

wherein $R_C$ is as indicated for each compound:

| Compound # | antibiotic | $R_C$ |
|---|---|---|
| 229 | eremomycin | D-Phe |
| 230 | eremomycin | L-Phe |
| 228 | eremomycin | Bn-O-L-Tyr |
| 203 | eremomycin | Lys |

-continued

| Compound # | antibiotic | $R_C$ |
|---|---|---|
| 242 (analog of #57) | eremomycin | $N^{\alpha}$-p-BuBn-L-Orn |
| 241 (analog of #220) | vancomycin | $N^{\alpha}$-p-$C_8H_{17}$-O-Bn-L-Orn |

TABLE 3a

Antibacterial activity of Eremomycin derivatives N'-substituted by non-glycine amino acids

| Cmpd/ Strain | 533 *S. epidermidis* | 602 *S. haemolyticus* | 3797 *S. aureus* (GISA) | 3798 *S. aureus* (GISA) | 568 *E. faecium* (GSE) | 559 *E. faecalis* (GSE) | 569 *E. faecium* (GRE) | 560 *E. faecalis* (GRE) |
|---|---|---|---|---|---|---|---|---|
| 229 | 1 | 1 | >32 | >32 | 0.25 | 0.5 | >64 | >64 |
| 230 | 4 | 4 | >32 | >32 | 2 | 2 | >64 | >64 |
| 228 | 4 | 4 | 16 | 16 | 2 | 2 | >64 | >64 |
| 203 | 0.13 | 0.13 | 4 | 8 | 0.25 | 0.25 | 16 | >64 |
| 242 | 0.25 | 1 | 4 | 4 | 0.5 | 1 | 8 | 8 |
| 241 | 0.5 | 1 | 2 | 2 | 1 | 1 | 16 | 16 |

TABLE 4

Double modified eremomycin derivatives of the formula:

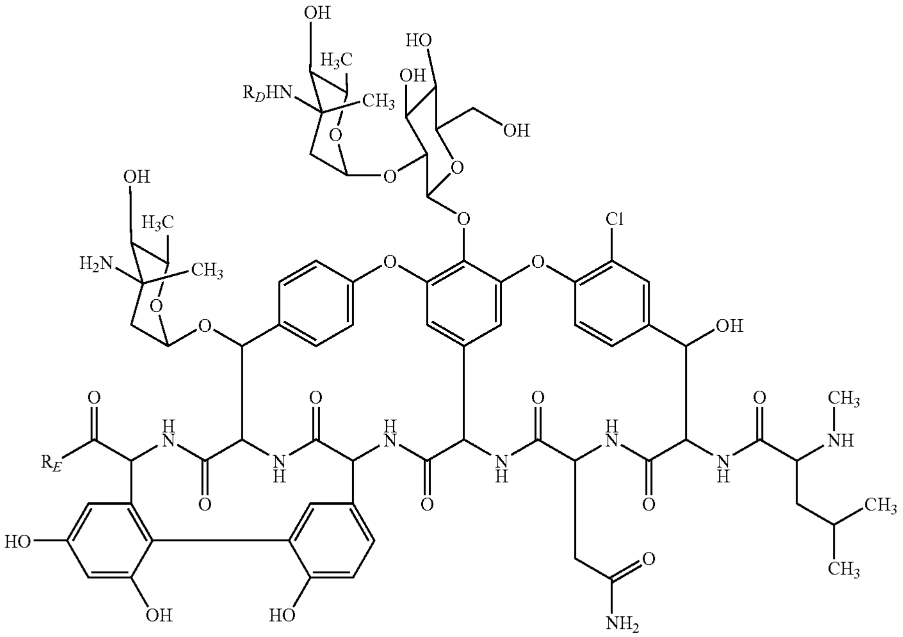

wherein $R_D$ and $R_E$ are as indicated for each compound:

| Compound # | $R_D$ | $R_E$ |
|---|---|---|
| 77 | p-BuBnHNCH$_2$CO | CH$_3$NH |
| 263 | p-BuBnHNCH$_2$CO | (Adam-2)NH |
| 264 | p-BuBnHNCH$_2$CO | (Adam-1)CH(CH$_3$)N |
| 265 | p-C$_8$H$_{17}$-OBnHNCH$_2$CO | (Adam-2)NH |

-continued

| Compound # | $R_D$ | $R_E$ |
|---|---|---|
| 266 | p-C$_8$H$_{17}$-OBnHNCH$_2$CO | (Adam-1)CH(CH$_3$)N |
| 275 | p-Cl-PhBnHNCH$_2$CO | p-F-BnNH |
| 213 | H | (Adam-2)NH |
| 262 | H | (Adam-1)CH(CH$_3$)N |

TABLE 4a

Antibacterial activity of double modified eremomycin derivatives

| Cmpd/ Strain | 533 *S. epidermidis* | 602 *S. haemolyticus* | 3797 *S. aureus* (GISA) | 3798 *S. aureus* (GISA) | 568 *E. faecium* (GSE) | 559 *E. faecalis* (GSE) | 569 *E. faecium* (GRE) | 560 *E. faecalis* (GRE) |
|---|---|---|---|---|---|---|---|---|
| 77 | 1 | 2 | 2 | 2 | 2 | 2 | 8 | 8 |
| 263 | 8 | 8 | 16 | 16 | 8 | 8 | 8 | 8 |
| 264 | 4 | 8 | 8 | 16 | 4 | 4 | 8 | 8 |
| 265 | 32 | 32 | >32 | >32 | n.t | n.t | n.t | n.t |
| 266 | 16 | 32 | >32 | >32 | n.t | n.t | n.t | n.t |
| 213 | 0.25 | 0.25 | 1 | 2 | 0.5 | 0.5 | 4 | 8 |
| 262 | 0.5 | 1 | 4 | 2 | 0.5 | 1 | 16 | 16 |

TABLE 5

Double modified vancomycin derivatives of the formula:

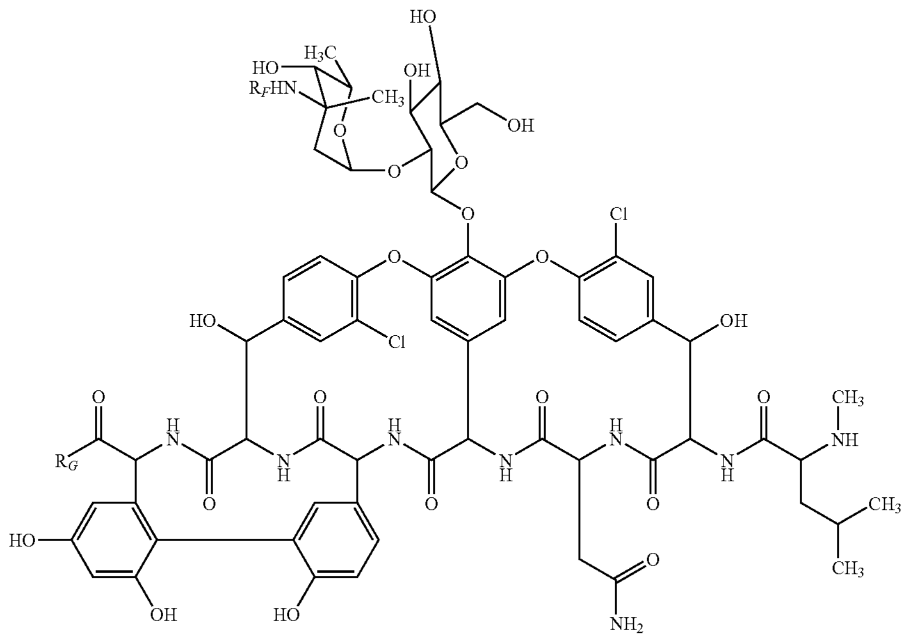

wherein $R_F$ and $R_G$ are as indicated for each compound:

| Compound # | $R_F$ | $R_G$ |
|---|---|---|
| 276 | p-BuBnHNCH$_2$CO | p-F-BnNH |
| 277 | p-C$_8$H$_{17}$-OBnHNCH$_2$CO | p-F-BnNH |
| 288 | H | p-F-BnNH |

TABLE 5a

Antibacterial activity of double modified vancomycin derivatives

| GINA/ Strain | 533 *S. epidermidis* | 602 *S. haemolyticus* | 3797 *S. aureus* (GISA) | 3798 *S. aureus* (GISA) | 568 *E. faecium* (GSE) | 559 *E. faecalis* (GSE) | 569 *E. faecium* (GRE) | 560 *E. faecalis* (GRE) |
|---|---|---|---|---|---|---|---|---|
| 276 | 0.5 | 2 | 2 | 2 | 2 | 4 | 16 | 16 |
| 277 | 4 | 8 | 8 | 4 | 4 | 4 | 8 | 8 |
| 288 | 2 | 1 | 4 | 4 | 0.13 | 0.13 | >64 | >64 |

CONCLUSION

Although the foregoing invention has been described in some detail for purposes of clarity of understanding, it will be apparent that certain changes and modifications may be practiced within the scope of the appended claims. It should be noted that there are many alternative ways of implementing both the processes and compositions of the present invention. Accordingly, the present embodiments are to be considered as illustrative and not restrictive, and the invention is not to be limited to the details given herein, but may be modified within the scope and equivalents of the appended claims.

What is claimed is:

1. The compound N'-p-BuBnHNCH$_2$CO eremomycin:

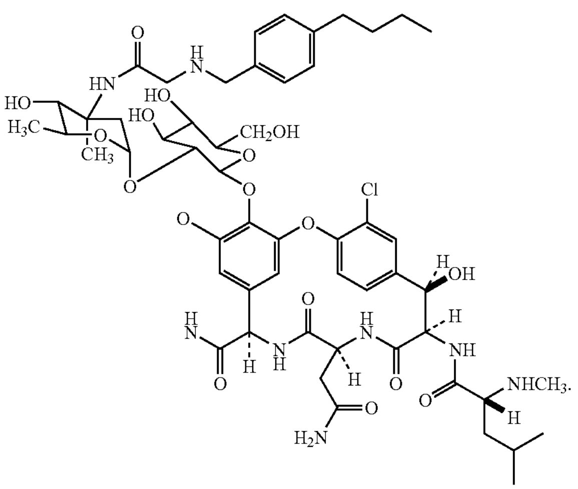

-continued

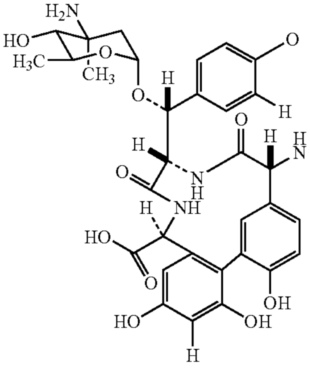

2. The compound N'-stilbenzylHNCH$_2$CO eremomycin.

3. A pharmaceutical composition comprising a therapeutically effective amount of the compound of claim 1, together with a pharmaceutically acceptable carrier.

4. A method of treating a bacterial infection in a mammal in need of such treatment comprising administering to the mammal an antibacterially effective amount of the compound of claim 1 together with a pharmaceutically acceptable carrier.

5. A method of making a compound of claim 1, comprising modifying an eremomycin scaffold,

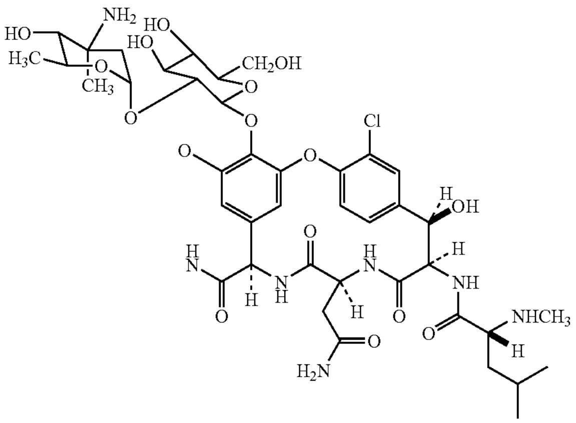

-continued

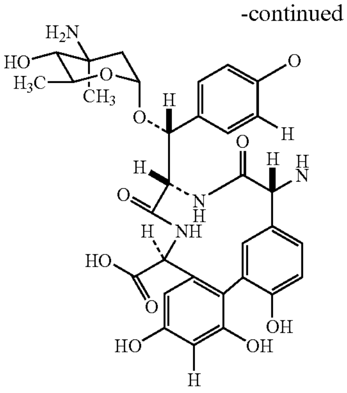

by acylation of the amino substituent on the amino-substituted sugar moiety of the eremomycin scaffold with an acyl group to form the compound of claim 1.

6. A method of making a compound of claim 2, comprising modifying an eremomycin scaffold,

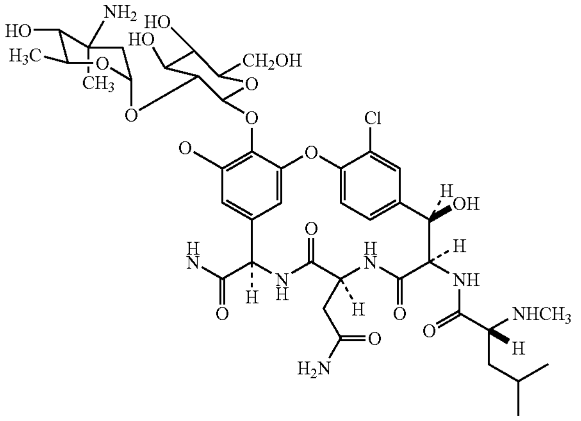

-continued

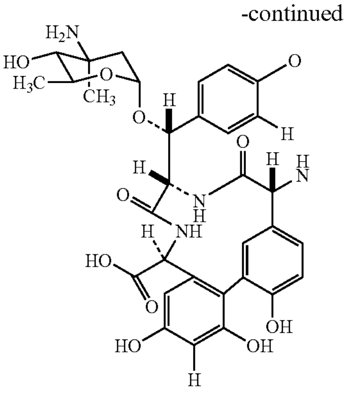

by acylation of the amino substituent on the amino-substituted sugar moiety of the eremomycin scaffold with an acyl group to form the compound of claim 2.

7. A pharmaceutical composition comprising a therapeutically effective amount of the compound of claim 2, together with a pharmaceutically acceptable carrier.

8. A method of treating a mammal in need of such treatment comprising administering to the mammal an antibacterially effective amount of the compound of claim 2 together with a pharmaceutically acceptable carrier.

* * * * *

UNITED STATES PATENT AND TRADEMARK OFFICE

CERTIFICATE OF CORRECTION

PATENT NO. : 7,632,918 B2
APPLICATION NO. : 11/361852
DATED : December 15, 2009
INVENTOR(S) : Chu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 584 days.

Signed and Sealed this

Second Day of November, 2010

David J. Kappos

*Director of the United States Patent and Trademark Office*